(12) United States Patent
DeCastro et al.

(10) Patent No.: US 10,591,364 B2
(45) Date of Patent: Mar. 17, 2020

(54) THERMAL CALIBRATION

(75) Inventors: Fernando DeCastro, Boyds, MD (US);
Renee Howell, Rockville, MD (US);
Sami Kanderian, Germantown, MD
(US); Johnathan S. Coursey,
Germantown, MD (US); **Kenton C.
Hasson, Germantown, MD (US); Scott
Sundberg**, Rockville, MD (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 13/223,258

(22) Filed: Aug. 31, 2011

(65) Prior Publication Data
US 2012/0178077 A1    Jul. 12, 2012

Related U.S. Application Data

(60) Provisional application No. 61/378,927, filed on Aug. 31, 2010, provisional application No. 61/378,591, filed on Aug. 31, 2010.

(51) Int. Cl.
| C12Q 1/68 | (2018.01) |
| --- | --- |
| G01K 11/06 | (2006.01) |
| G01K 15/00 | (2006.01) |
| B01L 7/00 | (2006.01) |
| B01L 3/00 | (2006.01) |
| C12Q 1/6806 | (2018.01) |
| C07H 21/04 | (2006.01) |

(52) U.S. Cl.
CPC ............ *G01K 11/06* (2013.01); *B01L 3/5027*
(2013.01); *B01L 7/52* (2013.01); *C12Q 1/6806*
(2013.01); *G01K 15/00* (2013.01); *B01L
2200/147* (2013.01); *B01L 2200/148*
(2013.01); *B01L 2300/0816* (2013.01); *B01L
2300/1827* (2013.01)

(58) Field of Classification Search
None
See application file for complete search history.

(56) References Cited

U.S. PATENT DOCUMENTS

| | | | |
| --- | --- | --- | --- |
| 5,599,668 A | 2/1997 | Stimpson et al. | |
| 7,629,124 B2 | 12/2009 | Hasson et al. | |
| 9,109,961 B2* | 8/2015 | Coursey | .................. G01K 15/00 |
| 2006/0223122 A1* | 10/2006 | Fogo | .................. G01N 33/5082 435/7.2 |
| 2006/0223197 A1* | 10/2006 | Vielsack | .............. G01N 33/533 436/524 |
| 2006/0234234 A1* | 10/2006 | Van Dongen | ......... C12Q 1/6886 435/6.12 |
| 2006/0246453 A1* | 11/2006 | Kato | .................. C12N 15/1096 435/6.11 |
| 2007/0026421 A1 | 2/2007 | Sundberg et al. | |
| 2008/0003593 A1 | 1/2008 | Hasson et al. | |
| 2009/0248349 A1 | 10/2009 | Hasson et al. | |
| 2010/0041044 A1 | 2/2010 | Wittwer et al. | |
| 2011/0048547 A1 | 3/2011 | Hasson et al. | |
| 2011/0056926 A1 | 3/2011 | Coursey | |
| 2012/0051390 A1* | 3/2012 | Coursey et al. | ................... 374/1 |
| 2013/0035248 A1* | 2/2013 | Icenhour | .............. C12Q 1/6895 506/9 |
| 2013/0040344 A1* | 2/2013 | Ju | ......................... C12Q 1/6853 435/91.21 |
| 2013/0040843 A1* | 2/2013 | Von Toerne | ........... C12Q 1/686 506/9 |
| 2013/0040847 A1* | 2/2013 | Thrippleton | ......... C12Q 1/6841 506/9 |

FOREIGN PATENT DOCUMENTS

| EP | 2 053 398 A1 | 4/2009 |
| --- | --- | --- |
| JP | 2006-503590 A | 2/2006 |
| JP | 2009-55858 A | 3/2009 |
| WO | 2009/158304 A2 | 12/2009 |
| WO | WO 2010019588 A1 * | 2/2010 |

OTHER PUBLICATIONS

"Human Genome Project," Wikipedia.com, accessed Jun. 7, 2013.*
"Human Hybrids," Michael F. Hammer, Scientific American, May 2013, pp. 66-71.*
"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Mar. 8, 2013).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*

(Continued)

*Primary Examiner* — Bradley L. Sisson
(74) *Attorney, Agent, or Firm* — Rothwell, Figg, Ernst & Manbeck, P.C.

(57) ABSTRACT

The present invention relates to the use of one or more amplicons as temperature calibrators. In some embodiments, the calibrators may be used to calibrate the temperature of a microfluidic channel in which amplification and/or melt analysis is performed. In some embodiments, the amplicons may be genomic, ultra conserved elements and/or synthetic. The amplicon(s) may have a known or expected melt temperature(s). The calibrators may be added to primers of study or may follow or lead the primers of study in the channel. The amplicon(s) may be amplified and melted, and the temperature(s) at which the amplicon(s) melted may be determined. The measured temperature(s) may be compared to the known temperature(s) at which the amplicon(s) was expected to melt. The difference(s) between the measured and expected temperatures may be used to calibrate/adjust one or more temperature control elements used to control and/or detect the temperature of the channel.

17 Claims, 26 Drawing Sheets

Specification includes a Sequence Listing.

(56) References Cited

OTHER PUBLICATIONS

"List of sequenced bacterial genomes" (Wikipedia.com; accessed Jan. 24, 2014).*
"Viruses", Wikipedia.com, accessed Nov. 24, 2012. (Year: 2012).*
"How many species of bacteria are there", wisegeek.com; accessed Jan. 21, 2014. (Year: 2014).*
"Fungi," Wikipedia.com; accessed Jun. 3, 2013. (Year: 2013).*
"Plant," Wikipedia.com; accessed Mar. 8, 2013. (Year: 2013).*
"Mammal," Wikipedia.com; accessed Sep. 22, 2011. (Year: 2011).*
"Murinae," Wikipedia.com, accessed Mar. 18, 2013. (Year: 2013).*
"Fish," Wikipedia.com, accessed Nov. 2, 2014. (Year: 2014).*
"Human Hybrids," Michael Hammer, Scientific American, May 2013, pp. 66-71. (Year: 2013).*
"List of sequenced animal genomes", Wikipedia.com (accessed Jan. 2018). (Year: 2018).*
PCT International Search Report and Written Opinion, issued in PCT/US 11/50104 dated Feb. 6, 2012, 23 pages.
Dodge, et al., "A Microfluidic Platform Using Molecular Beacon-Based Temperature Calibration for Thermal Dehydridization of Surface-Bound DNA," Anal. Chem., vol. 76, pp. 1778-1787 (Mar. 15, 2004).
Scaruffi, et al., "Transcribed-ultra conserved region expression profiling from low-input total RNA," BMC Genomics, vol. 11, document 149 (2010).
Kinahan, et al., "Effect of substrate thermal resistance on space-domain microchannel fluorescent melting curve analysis," Biomed Microdevices, vol. 11, No. 4, pp. 747-754 (Mar. 4, 2009).
Dodge, A., et al. "A Microfluidic Platform Using Molecular Beacon-Based Temperature Calibration for Thermal Dehydridization of Surface-Bound DNA," Analytical Chemistry, vol. 76, No. 6, pp. 1778-1787 (Mar. 15, 2004).
Bejerano, G., et al. "Ultraconserved Elements in the Human Genome," Science, vol. 304, pp. 1321-1325 (May 28, 2004).
Database EMBL [online], "CH230-225C7.TV CHORI-230 Segment 1 Rattus norvegicus genomic clone CH230-225C7, DNA sequence", XP-002771624, retrieved from EBI accessing No. EM_GSS:BZ100576 Database accessing No. BZ100576.

* cited by examiner

Overall Results for sample 1: A
Number of peaks found: 1
Peak table for sample 1: A

| Peak | Size [bp] | Conc. [ng/µl] | Molarity [nmol/l] | Observations |
|---|---|---|---|---|
| 1 | ◁ 15 | 4.20 | 424.2 | Lower Marker |
| 2 | 113 | 13.22 | 177.8 | |
| 3 | ▷ 1,500 | 2.10 | 2.1 | Upper Marker |

Overall Results for sample 3: B
Number of peaks found: 2
Peak table for sample 3: B

| Peak | Size [bp] | Conc. [ng/μl] | Molarity [nmol/l] | Observations |
|---|---|---|---|---|
| 1 | ◁ 15 | 4.20 | 424.2 | Lower Marker |
| 2 | 204 | 0.49 | 3.6 | |
| 3 | 209 | 97.77 | 707.7 | |
| 4 | ▷ 1,500 | 2.10 | 2.1 | Upper Marker |

Cal Melt (calibrated)

Cal Check Melt

THERMAL CALIBRATION

CROSS-REFERENCE TO RELATED APPLICATIONS

The present application claims the benefit of priority to U.S. Provisional Application Ser. No. 61/378,927, filed on Aug. 31, 2010, the entire disclosure of which is incorporated herein by reference. In addition, the present application claims the benefit of priority to U.S. Provisional Application Ser. No. 61/378,591, filed on Aug. 31, 2010, the entire disclosure of which is incorporated herein by reference.

SEQUENCE SUBMISSION

The present application is being filed along with a Sequence Listing in electronic format. The Sequence Listing is entitled 3400233 SequenceListing.txt, was created on Aug. 30, 2011 and is 11 kb in size. The information in the electronic format of the Sequence Listing is part of the present application and is incorporated herein by reference in its entirety.

BACKGROUND

Field of the Invention

The present invention relates to methods, devices, and systems for calibrating a temperature of one or more microfluidic channels in a microfluidic device. More particularly, aspects of the present invention relate to methods, devices, and systems for using an amplicon having a known or expected thermal melting temperature to calibrate a thermal sensor and/or thermal control element used to control the temperature of a microfluidic channel in a microfluidic device. The present invention also relates to methods, devices and systems for calibrating the temperature of a thermal melt in a microfluidic channel of a microfluidic device. More particularly, aspects of the present invention relate to methods, devices, and systems for using a calibrant present in a test sample and amplifying the calibrant to produce a calibrant amplicon in which the calibrant amplicon has a known or expected thermal melting temperature to calibrate the melting temperature of an amplicon of a nucleic acid of interest. The present invention also relates to the use of a calibrant present in a test sample as a control for determining whether amplification of a sample has occurred.

Description of the Background

Devices for performing chemical, biological, or other reactions (e.g., a microfluidic device for performing polymerase chain reaction (PCR) amplification of DNA molecules, or a microfluidic molecular diagnostic platform that performs PCR on a patient sample and then uses the PCR product for genotyping by performing a high resolution melt analysis) often feature one or more thermal control elements that are used to subject reactants to a desired thermal profile. A description of PCR amplification, and an example of one possible microfluidic device including thermal control elements for PCR amplification and thermal melt analysis, are provided in U.S. Patent Application Publication Nos. 2009/0248349 and 2011/0056926, the entire disclosures of which are incorporated herein by reference.

In many applications of such microfluidic devices (e.g., PCR and/or thermal melt analysis), the thermal control elements of those devices must be precisely calibrated. That is, the correspondence between the temperature of the thermal control element and an electrical characteristic of the thermal control element must be precisely determined. For example, in the case of a resistance temperature detector and/or heater, the correspondence between temperature and resistance must be precisely determined. Additional types of thermal control elements can include platinum resistive heaters, thermistors, diode temperature sensors, thermocouples, or any other suitable temperature measuring devices. Additional electrical characteristics of thermal control elements that correspond to temperature can include capacitance or inductance of an element, frequency, pulse width, or amplitude of a signal, or other sensor characteristics known in the art.

Among many variations that can occur in microfluidic devices, temperature variation between channels is particularly relevant. Securing the right and uniform temperature among channels in a microfluidic device or chip leads to a reliable and consistent PCR and thermal melt analysis. In turn, having a successful amplification and melt of the target sequence may lead to a correct sample genotyping, which may lead to the characterization of a patient with a genetic disorder or a genetic predisposition or the efficiency of drug metabolism.

As noted above, assuring that microfluidic channels in a chip present the same temperature during a PCR and thermal melt analysis reaction will result in improved reliability and consistency. However, with such small elements and such small volumes of reagents, it is very challenging to test and prove that channels at the same time are performing a PCR plus thermal melting under the same optimal temperature conditions.

Methods of calibrating thermal control elements of a microfluidic device often include generating a lookup table or a series of coefficients that define a calibration equation, i.e., a lookup table or an equation relating the temperature of the thermal control element with the electrical characteristic.

Calibration can be performed by sending the device to a third party laboratory for taking accurate measurements and generating the lookup table or series of coefficients; however, this procedure is generally expensive and time consuming. Furthermore, for many devices (e.g., many common microfluidic devices) there may be many thermal control elements (e.g. dozens or even hundreds of heaters and sensors), each of which requires its own precise calibration, making third-party calibration impractical.

Accordingly, there is a need in the art for a reliable calibrant that will be useful in calibrating the temperature of one or more microfluidic channels in a microfluidic device or chip. Similarly, there is a need for robust calibration of thermal sensors and/or heaters that can be accurate, reduce downtime and maintain high throughput.

SUMMARY

In one aspect, the present invention provides a method of calibrating the temperature of a microfluidic channel present in a microfluidic system comprising a controller. The method may comprise: (a) introducing into the microfluidic channel reagents including one or more amplicons; (b) melting the one or more amplicons and determining a melting temperature of each of the one or more amplicons; (c) comparing the determined melting temperature of each of the one or more amplicons with a respective expected melting temperature of each of the one or more amplicons; and (d) adjusting the controller based on the comparison of the determined melting temperature of each of the one or more amplicons with the respective expected melting temperature of each of the one or more amplicons.

In some embodiments, one or more of the one or more amplicons are prepared synthetically and then introduced into the microfluidic channel. In some embodiments, the one or more amplicons may be prepared from genomic DNA. In some embodiments, the amplicons may be prepared from Ultra Conserved Elements (UCEs). In other embodiments, the amplicons may be prepared from any coding sequences, such as sickle cell coding sequence. In other embodiments, the one or more amplicons may be prepared from any synthetic DNA. In additional embodiments, the one or more amplicons may be prepared from both genomic DNA or synthetic DNA. In some embodiments, one of the one or more amplicons may be prepared from RFCAL-100. In other embodiments, one of the one or more amplicons may be prepared from RFCAL-200. In additional embodiments, the amplicons may be prepared from both RFCAL-100 and RFCAL-200. The controller may control and/or detect the temperature of the microfluidic channel.

In one embodiment, the microfluidic channel reagents may include at least two amplicons; the melting and determining may comprise melting the two or more amplicons and determining a melting temperature of each of the two more amplicons; the comparing may comprise comparing the determined melting temperature of each of the two or more amplicons with a respective expected melting temperature of each of the two or more amplicons; and the adjusting may comprise adjusting the controller based on the comparison of the determined melting temperature of each of the two or more amplicons with the respective expected melting temperature of each of the two or more amplicons. The two or more amplicons may have known melting temperatures more than 5 degrees Celsius apart. The two or more amplicons may have known melting temperatures more than 10 degrees Celsius apart. The two or more amplicons may have known melting temperatures more than 15 degrees Celsius apart. The two or more amplicons have known melting temperatures more than 20 degrees Celsius apart.

In some embodiments, the determining the melting temperature of each of the two or more amplicons may comprise: obtaining a derivative of a melt curve of the melting of the two or more amplicons using a Savitzky-Golay filter, and finding the temperatures at the maximum negative derivatives of the derivative of the melt curve. The determining the melting temperature of each of the two more amplicons may comprise: cross-correlating peaks of a derivative of a reference melt curve against peaks of a derivative of a melt curve of the melting of the two or more amplicons, and selecting the temperatures having the highest correlation as the melting temperatures of the two more amplicons. The comparing the determined melting temperature of each of the two or more amplicons with the respective expected melting temperature of each of the two or more amplicons may comprise calculating a slope correction factor and an intercept correction factor using the respective expected melting temperature of each of the two or more amplicons. The adjusting the controller may comprise calculating an adjusted temperature using the calculated slope correction factor and the calculated intercept correction factor.

In one embodiment, a derivative of a melt curve of the melting of the one or more amplicons may exhibit a single peak, for instance where only one amplicon is used. The melting of the one or more amplicons may comprise a first melting of the one or more amplicons and a second melting of the one or more amplicons. The determining the melting temperature of each of the one or more amplicons may comprise (i) determining a first temperature corresponding to a peak of the derivative of the melt curve of the first melting of the one or more amplicons and (ii) determining a second temperature corresponding to a peak of the derivative of the melt curve of the second melting of the one or more amplicons. The adjusting the controller may comprise calculating a temperature adjustment using a linear interpolation of the first and second temperatures.

In another aspect, the present invention provides a method of calibrating the temperature of a thermal melt in a microfluidic channel present in a microfluidic system. The method may comprise: (a) introducing into the microfluidic channel reagents comprising a test sample containing human genomic DNA, at least a pair of primers for one or more nucleic acids of interest and a pair of primers for a calibrant, wherein the calibrant is found in genomic DNA; (b) amplifying the genomic DNA to produce a calibrant amplicon and an amplicon of the at least one nucleic acid of interest; (c) melting the amplicons and determining a melting temperature of each of the amplicons; (d) comparing the determined melting temperature of the calibrant amplicon with an expected melting temperature of the calibrant amplicon; and (e) calibrating the melting temperature of the amplicon of the at least one nucleic acid of interest based on the melting temperature of the calibrant amplicon.

It is within the scope of the invention that segments of fluid may be added to the microfluidic channel sequentially. Each segment of fluid may be of different composition than a segments directly adjacent to it. In one embodiment, the pair of primers for the calibrant may be added to the microfluidic channel in a separate fluid segment ("calibrant fluid segment") than the at least one pair of primers for the one or more nucleic acids of interest ("assay fluid segment"). In some embodiments, one or more calibrant fluid segments may be added to the microfluidic channel prior to multiple assay fluid segments being added to the microfluidic channel. In other embodiments, one or more calibrant fluid segments may be added to the microfluidic channel before multiple assay fluid segments are added to the microfluidic channel, and one or more calibrant fluid segments may be added after the assay fluid segments. In other embodiments, calibrant fluid segments may alternate with assay fluid segments such that each assay fluid segment has a calibrant fluid segment adjacent on either side. It is therefore noted that throughout the specification, the introduction of at least one pair of primers for the one or more nucleic acids of interest and the introduction of the pair of primers for the calibrant into the microfluidic channel can occur in the same or in separate fluid segments, wherein the separate fluid segments may be introduced in any order, alternately, sequentially, or at the start and end of multiple fluid segments.

In some embodiments, the microfluidic channel reagents include a pair of primers for one nucleic acid of interest. As used herein, nucleic acid of interest refers to a nucleic acid whose presence or absence is to be determined in a test sample. In other embodiments, the microfluidic channel reagents include a pair of primers for each of two or more nucleic acids of interest. In some embodiments, the calibrant found in genomic DNA is a DNA segment that is known to be present in all genomic DNA of interest, such as human genomic DNA. In other embodiments, the calibrant is a UCE. In some embodiments, the microfluidic channel reagents may contain a pair of primers for the calibrant. In certain embodiments, the amplification of the microfluidic reagents produce a calibrant amplicon. In certain embodiments, the amplification of the calibrant dos not affect amplification of the one or more nuclei acids of interest.

In some embodiments, the determining the melting temperature of each of the amplicons may comprise: obtaining a derivative of a melt curve of the melting of the amplicons using a Savitzky-Golay filter, and finding the temperatures at the maximum negative derivatives of the derivative of the melt curve. The determining the melting temperature of each of the amplicons may comprise: cross-correlating peaks of a derivative of a reference melt curve against peaks of a derivative of a melt curve of the melting of the amplicons, and selecting the temperatures having the highest correlation as the melting temperatures of the amplicons. The comparing the determined melting temperature of the calibrant amplicon with the respective expected melting temperature of the calibrant amplicon may comprise calculating a slope correction factor and an intercept correction factor using the respective expected melting temperature of the calibrant amplicon. Calibrating the melting temperature of each of the amplicons of the nucleic acids of interest may comprise calculating an adjusted temperature using the calculated slope correction factor and the calculated intercept correction factor of the calibrant amplicon.

The method may comprise using the comparison of the determined melting temperature of the calibrant amplicon with the respective expected melting temperature of the calibrant amplicon to validate amplification of the one or more amplicons of the one or more nucleic acids of interest. The validation may comprise determining the corrected melting temperatures of the amplicons of the nucleic acids of interest.

The method may also comprise using the melt curve of the calibrant amplicon as a control to validate amplification has occurred. Obtaining a melt curve for the calibrant can serve as a positive control to demonstrate that no contamination of the reagents or other anomalies have occurred that would prevent amplification of the genomic DNA.

In another aspect, the present invention provides a method of calibrating the temperature of a microfluidic channel. The method may comprise: performing in the microfluidic channel a thermal melt analysis of at least one amplicon having a known thermal melting temperature and adjusting a thermal control element based on a deviation of the thermal melting temperature from the known value.

In still another aspect, the present invention may provide a calibrant comprising RFCAL-100.

In yet another aspect, the present invention may provide a calibrant comprising RFCAL-200. The calibrant may further comprise RFCAL-100.

In another aspect, the present invention provides a calibrant (a) which is present in human genomic DNA, (b) amplification of which produces an amplicon having a known melting temperature that does not interfere with the amplification of one or more nucleic acids of interest that may be present in the human genomic DNA.

The above and other aspects and features of the present invention, as well as the structure and application of various embodiments of the present invention, are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF THE PREFERRED EMBODIMENTS

Figure 1:
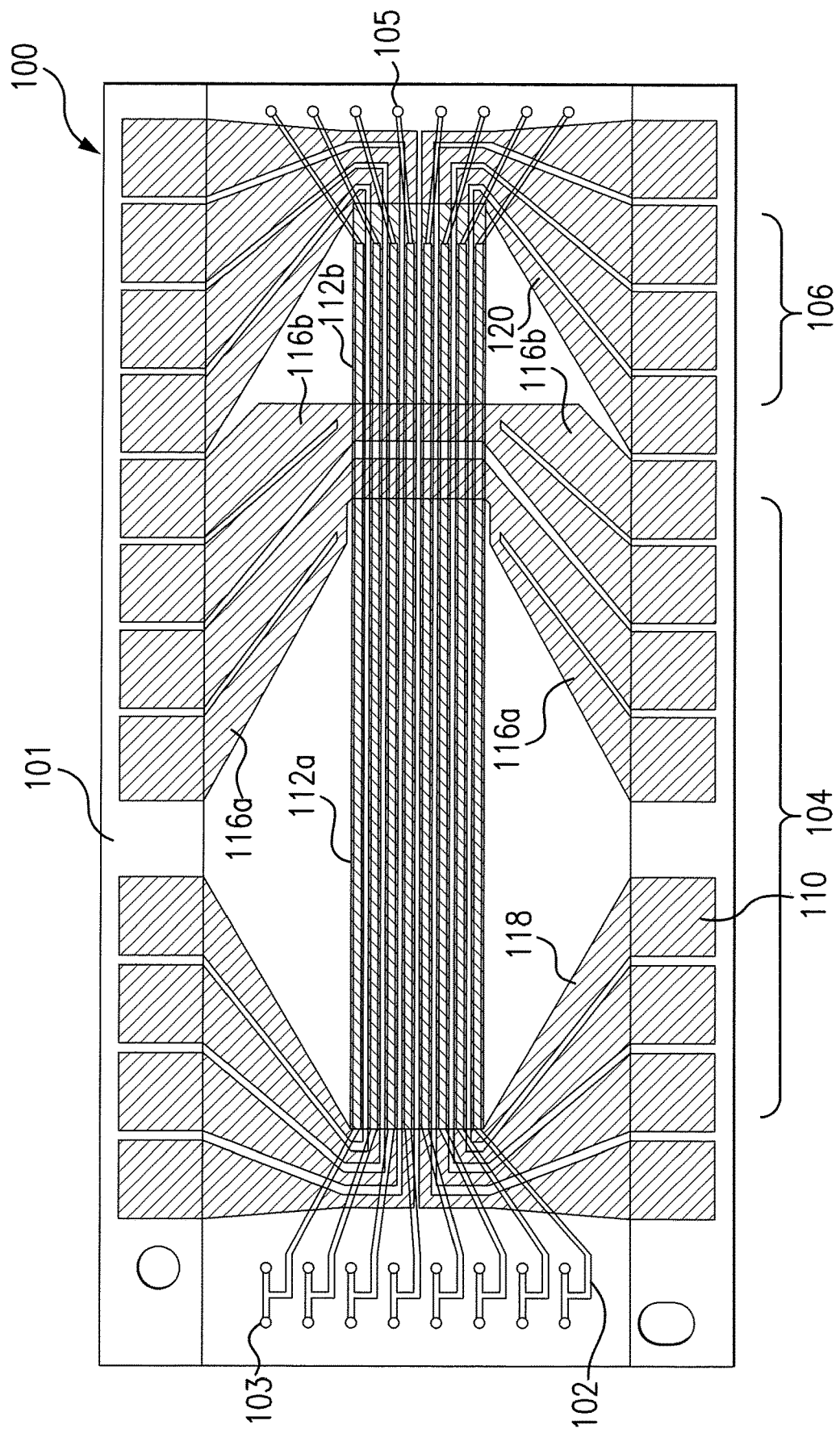
FIG. 1 illustrates a microfluidic device embodying aspects of the present invention.

FIG. 1 illustrates a microfluidic device 100 embodying aspects of the present invention. As described herein, the microfluidic device 100 may also be referred to interchangeably as the reaction chip or as the U-chip. In the illustrated embodiment, the microfluidic device 100 includes several microfluidic channels 102 extending across a substrate 101. Each channel 102 includes one or more inlet ports 103 (the illustrated embodiment shows two inlet ports 103 per channel 102) and one or more outlet ports 105 (the illustrated embodiment shows one outlet port 105 per channel 102). In exemplary embodiments, each channel may be subdivided into a first portion extending through a PCR thermal zone 104 (as described below) and a second portion extending through a thermal melt zone 106 (as described below).

In an embodiment, the microfluidic device 100 further includes thermal control elements in the form of thin film resistive heaters 112 associated with the microfluidic channels 102. In one non-limiting embodiment, the thin film resistive heaters 112 may be platinum resistive heaters whose resistances are measured in order to control their respective temperatures. In the embodiment illustrated in FIG. 1, each heater element 112 comprises two heater sections: a PCR heater 112a section in the PCR zone 104, and a thermal melt heater section 112b in the thermal melt zone 106.

In one embodiment, the microfluidic device 100 includes a plurality of heater electrodes 110 connected to the various thin-film heaters 112a and 112b. In non-limiting embodiments, heater electrodes 110 may include PCR section leads 118, one or more PCR section common lead 116a, thermal melt section leads 120, and one or more thermal melt section common lead 116b. According to one embodiment of the present invention, a separate PCR section lead 118 is connected to each of the thin-film PCR heaters 112a, and a separate thermal melt section common lead 120 is connected to each of the thin-film thermal melt heaters 112b.

Figure 2:
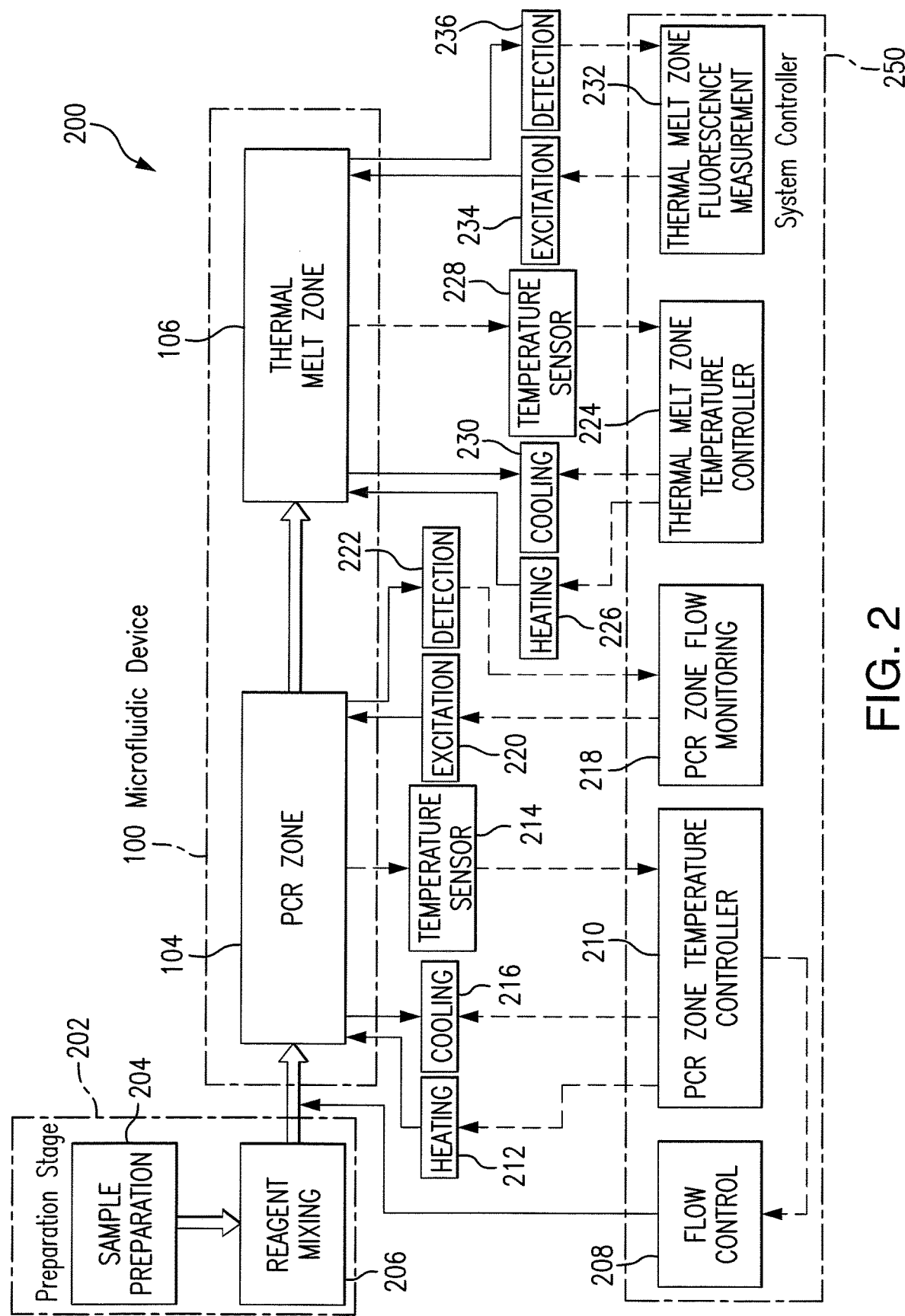
FIG. 2 is a functional block diagram of a system for using a microfluidic device embodying aspects of the present invention.

FIG. 2 illustrates a functional block diagram of a system 200 for using a microfluidic device 100, in accordance with one embodiment. The DNA sample is input in the microfluidic chip 100 from a preparation stage 202. As described herein, the preparation stage 202 may also be referred to interchangeably as the pipettor system or as the pre-K stage. The preparation stage 202 may comprise appropriate devices for preparing the sample 204 and for adding one or more reagents 206 to the sample. Once the sample is input into the microfluidic chip 100, e.g., at an input port 103, the sample flows through a channel 102 into the PCR zone 104 where PCR takes place. That is, as explained in more detail below, as the sample flows within a channel 102 through the PCR zone 104, the sample is exposed to the PCR temperature cycle a plurality of times to effect PCR amplification. Next, the sample flows into the thermal melt zone 106 where a high resolution thermal melt process occurs. Flow of sample into the microfluidic chip 100 can be controlled by a flow controller 208. The flow controller may be part of a control system 250 of the system 200. The control system 250 may comprise the flow controller 208, a PCR zone temperature controller 210, a PCR flow monitor 218, a thermal melt zone temperature controller 224, and/or a zone fluorescence measurement system 232.

The temperature in the PCR zone 104 can be controlled by the PCR zone temperature controller 210. The PCR zone temperature controller 210, which may be a programmed computer or other microprocessor, sends signals to the heater device 212 (e.g., a PCR heater 112a) based on the temperature determined by a temperature sensor 214 (such as, for example, an RTD or thin-film thermistor, or a thin-film thermocouple thermometer). In this way, the temperature of the PCR zone 104 can be maintained at the desired level. According to some embodiments of the present invention, the PCR zone 104 may also be cooled by a cooling device 216 (for example, to quickly bring the channel temperature from 95° C. down to 55° C.), which may also be controlled by the PCR zone temperature controller 210. In one embodiment, the cooling device 216 could be a peltier device, heat sink or forced convection air cooled device, for example.

The flow of sample through the microfluidic channels 102 can be measured by a PCR zone flow monitoring system 218. In one embodiment, the flow monitoring system can be a fluorescent dye diffusion imaging and tracking system illustrated in U.S. Pat. No. 7,629,124, which is incorporated herein by reference in its entirety. According to one embodiment of the present invention, the channels in the PCR zone can be excited by an excitation device 220 and light fluoresced from the sample can be detected by a detection device 222. An example of one possible excitation device and detection device forming part of an imaging system is illustrated in U.S. Patent Application Publication No. 2008/0003593 and U.S. Pat. No. 7,629,124, which are incorporated herein by reference in their entirety.

The thermal melt zone temperature controller 224, e.g. a programmed computer or other microprocessor, can be used to control the temperature of the thermal melt zone 106. As with the PCR zone temperature controller 210, the thermal melt zone temperature controller 224 sends signals to the heating component 226 (e.g., a thermal melt heater 112b) based on the temperature measured by a temperature sensor 228 which can be, for example, an RTD or thin-film thermocouple. Additionally, the thermal melt zone 106 may be independently cooled by cooling device 230. The fluorescent signature of the sample can be measured by the thermal melt zone fluorescence measurement system 232. The fluorescence measurement system 232 excites the sample with an excitation device 234, and the fluorescence of the sample can be detected by a detection device 236. An example of one possible fluorescence measurement system is illustrated in U.S. Patent Application Publication No. 2008/0003593 and U.S. Pat. No. 7,629,124, which are incorporated herein by reference in their entirety.

In accordance with aspects of the present invention, the thin film heaters 112 may function as both heaters and temperature detectors. Thus, in one embodiment of the present invention, the functionality of heating element 212 and 226 and temperature sensors 214 and 228 can be accomplished by the thin film heaters 112.

In one embodiment, the system 200 sends power to the thin-film heaters 112a and/or 112b, thereby causing them to heat up, based on a control signal sent by the PCR zone temperature controller 210 or the thermal melt zone temperature controller 224. The control signal can be, for example, a pulse width modulation (PWM) control signal. An advantage of using a PWM signal to control the heaters 212 is that with a PWM control signal, the same voltage potential across the heaters may be used for all of the various temperatures required. In another embodiment, the control signal could utilize amplitude modulation or alternating current. It may be advantageous to use a control signal that is amplitude modulated to control the heaters 212 because a continuous modest change in voltage, rather than large voltage steps, avoids slew rate limits and improves settling time. Further discussion of amplitude modulation can be found in U.S. Patent Application Publication No. 2011/0048547, which is incorporated herein by reference in its entirety. In some embodiments, the desired temperature for the heaters is reached by changing the duty cycle of the control signal. For example, in one non-limiting embodiment, the duty cycle of the control signal for achieving 95° C. in a PCR heater might be about 50%, the duty cycle of the control signal for achieving 72° C. in a PCR heater might be about 25%, and the duty cycle of the control signal for achieving 55° C. in a PCR heater might be about 10%. In other embodiments, other duty cycles may be used as would be apparent to persons skilled in the art.

The microfluidic device 100 and the system 200 can be used in conjunction with aspects of the present invention. For example, the system 200 may calibrate the thermal control elements 112 of the microfluidic device 100 using an amplicon having a known or expected thermal melting temperature, in accordance with aspects of the invention. However, an amplicon having a known or expected thermal melting temperature may be used to calibrate thermal control elements in microfluidic devices and systems other than the microfluidic device 100 and the system 200 illustrated in the FIGS. 1 and 2.

Figure 18A:
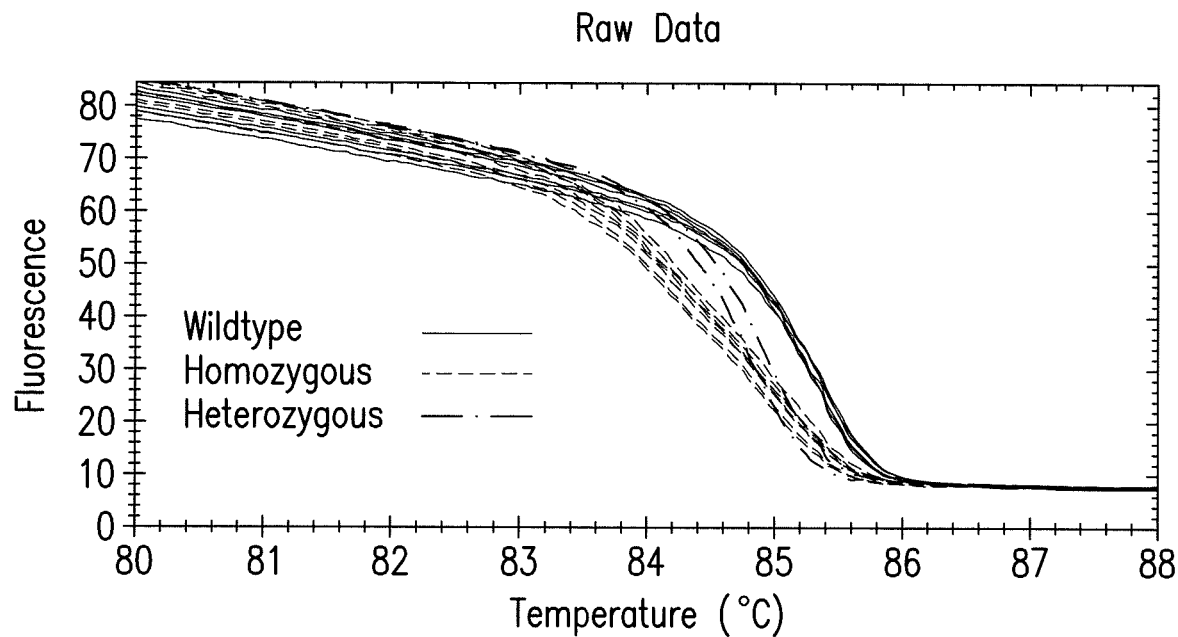
FIG. 18A illustrates fluorescence versus temperature melt curves for Warfarin CyP2C9*2.
Figure 18B:
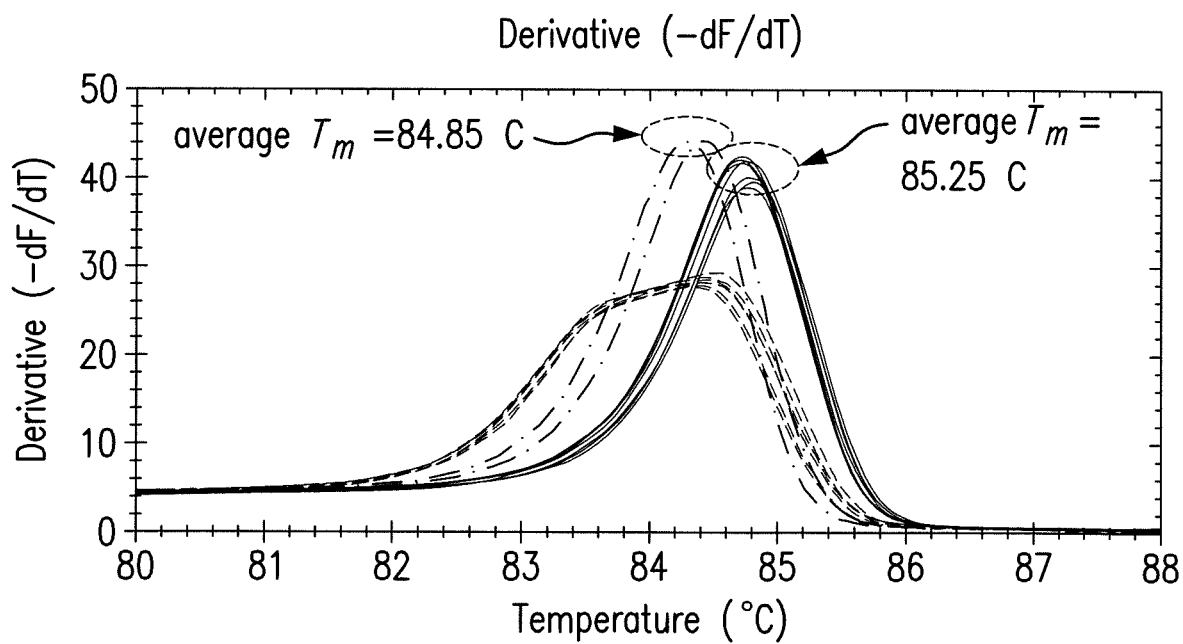
FIG. 18B illustrates derivative of fluorescence with respect to temperature melt curves for Warfarin CyP2C9*2.

In high resolution thermal melting instruments, such as system 200, temperature precision is of extreme importance. For example, a small bias or shift in temperature may cause a genotype misclassification when analyzing melt curves. Whether analyzing fluorescence versus temperature or derivative of fluorescence with respect to temperature, a homozygous DNA sample containing a single nucleotide polymorphism and a wildtype DNA sample have the same shape and only differ by a small temperature shift. For example, FIG. 18A illustrates fluorescence versus temperature melt curves for Warfarin CyP2C9*2, and FIG. 18B illustrates the derivative of fluorescence with respect to temperature melt curves for Warfarin CyP2C9*2. As shown in FIG. 18B, the temperature difference between the two profiles, or average difference in true melting temperature, is only 0.4° C. For such genotypes that exhibit the same shape and only differ by a shift, the melting temperature of the DNA, $T_m$, estimated by the peak temperature of the derivative is often used to classify the genotypes. A small drift or bias in measured temperature may increase the misclassification of these genotypes. If there is a positive temperature shift or drift, a homozygous mutant can be misclassified as a wildtype. Conversely, if there is a negative temperature shift or drift, a wildtype can be misclassified as homozygous mutant.

A temperature shift may be due to spatial differences in temperature such as in a well plate (gradient), or a shift in time (drift). In an ideal system, where there are no temperature shifts, or biases in measured temperature in space or time, there would be a much lower variance in melting temperatures for a particular genotype. However, in real instruments, temperature gradients and drift are real phenomena.

One aspect of the present invention is the calibration of the temperature of a microfluidic channel (e.g., channel 102) of a microfluidic device (e.g., device 100). In some embodiments, the calibration may be performed by calibrating one or more thermal control elements (e.g., thin film resistive heaters 112) that control and/or detect the temperature of a microfluidic channel. In some embodiments, the temperature of a plurality of microfluidic channels (e.g., channel 102) may be calibrated. In some embodiments, the calibration may be performed using a single amplicon having a known or expected thermal melting temperature as a calibrant. The amplicon is introduced into the thermal melting zone of the microfluidic channels and the amplicon is melted. In one embodiment, the amplicon may be derived from genomic DNA. In one particular embodiment, the amplicon may be produced from an Ultra Conserved Element (UCE). In an alternative embodiment, the amplicon may be produced from a synthetic DNA. In a further embodiment, the amplicon may be produced from coding sequences, such as a sickle cell coding sequence.

In some embodiments, the calibration may be performed using a two or more amplicons each having a known or expected thermal melting temperature. In particular embodiments, the two or more amplicons may be produced from genomic DNA, synthetic DNA or a combination of one or more amplicon derived from genomic DNA and one or more synthetic amplicons. In addition, one or more of the two or more amplicons may be UCEs.

Figure 3A:
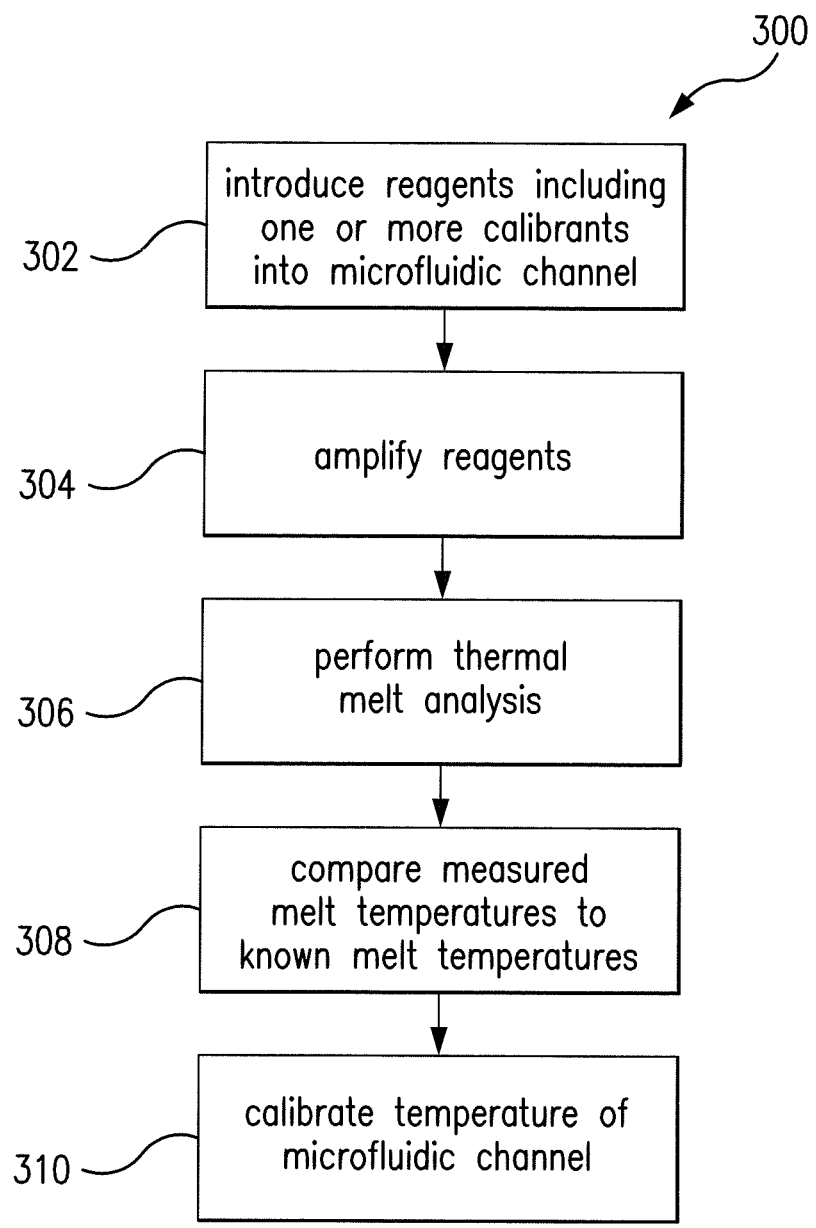
FIG. 3A is a flow chart illustrating a process for calibrating the temperature of a microfluidic channel of a microfluidic device in accordance with an embodiment of the present invention.

FIG. 3A illustrates a process 300a for calibrating the temperature of a microfluidic channel of a microfluidic device in accordance with an embodiment of the present invention. The process 300a may begin at step 302 at which amplicons are introduced into the microfluidic channel. In a preferred embodiment, each one of the one or more amplicons has a known thermal melting temperature. In other words, in a preferred embodiment, the temperature at which each of the one or more amplicons is expected to melt is known. In one embodiment, the one or more amplicons comprise any synthetic sequence.

At step 304, a thermal melt analysis may be performed on the amplification product. In other words, the amplicons may be melted, and the temperature at which the amplicons melt may be measured. In this way, the process 300a may determine the temperature at which each one of the one or more amplicons in a microfluidic channel melted. In one embodiment, the thermal melt analysis may be performed by exposing the amplicons to a temperature ramp. The amplicons may be exposed to the temperature ramp (e.g., heating the thermal control element at, for example, 0.5 degrees Celsius per second over a range of temperatures that includes temperatures corresponding to the features of the thermal response profiles of the amplicons) in a thermal melt zone of a microfluidic device (e.g., thermal melt zone 106 of microfluidic device 100). During the thermal ramp, a dependent variable (e.g., fluorescence intensity) of the amplicons and the measurement value of the thermal control element is monitored to generate a thermal response profile. The temperature may be measured by a thermal melt zone fluorescence measurement system (e.g., thermal melt zone fluorescence measurement system 232). However, any known method and/or device for performing thermal melt analysis may be used.

In one embodiment, thermal melt analysis may be an analysis of a dependent variable related to a solution (e.g., reagent solution) that is subject to a thermal variation, i.e., the relationship between a solution's temperature and the dependent variable. In some embodiments, the thermal response profile may be a melt curve, i.e. the fluorescent melt analysis of a solution to determine the relationship between the amount of fluorescence and the solution's temperature. In some embodiments, generating such a thermal response profile can include loading a microfluidic chip (e.g., the microfluidic chip 100) into a system for controlling reactions in the microfluidic chip (e.g., system 200), loading a droplet, plug, slug, or continuous flow of the reagents including the one or more amplicons into the chip (e.g., into a microfluidic channel 102), and controlling a thermal control element (e.g., heater 112) that is in thermal communication with the amplicons to heat the amplicons while monitoring the temperature of the thermal control element and while monitoring the dependent variable (e.g., fluorescence in the case in which a melt curve is obtained) of the amplification product.

In one embodiment, the apparent (i.e., measured) temperatures of each feature (e.g., the apparent melt temperature corresponding to each amplicon) may be identified from a thermal response profile. In some embodiments, the apparent temperatures may be determined from the derivative plot using peak-picking. In other embodiments, the apparent temperatures may be determined by cross-correlating the derivative plot with a known template (i.e., an expected thermal response profile) for each amplicon, or shifting and stretching the thermal response profile to match a predefined template.

At step 306, for each of the one or more amplicons, the measured temperature at which the amplicon melted is compared to the known (i.e., expected) thermal melt temperature for the amplicon. The comparison may be performed by, for example, a digital or analog comparator. The comparator may be part of a control system of a microfluidic system (e.g., control system 250 of system 200). However, any known method and/or device for performing the comparison may be used.

At step 308, the temperature of the microfluidic channel is calibrated based on the results of the comparison(s) of the measured melt temperature(s) to the respective known thermal melt temperature(s). The calibration may be performed by adjusting a controller (e.g., control system 250) and/or one or more thermal control elements (e.g., heater 112) that control and/or detect the temperature of the microfluidic channel (e.g., channel 102).

In some embodiments, calibration of a thermal control element can include determining the coefficients of a calibration equation, i.e., an equation that models the relationship between the temperature of the thermal control element and a measurement value. In an embodiment, that measurement value may be an electrical characteristic of the thermal control element. For example, a calibration equation for a resistive heater 112 may model the relationship between the temperature of the heater 112 and the resistance of the heater 112. In this embodiment, the calibration equation may model a linear relationship as shown in Equation 1:

$$T = k_0 + k_1 R \quad \text{Equation 1}$$

In this case, T is temperature of the thermal control element, R is the resistance of the thermal control element, and $k_0$ and $k_1$ are constants (i.e., the coefficients) to be determined by calibration. Two calibration coefficients can be determined by, for example, measuring the resistance R at two known temperatures ($T_1$ and $T_2$). In some aspects of the present invention, these measurements can be obtained by heating the thermal control element (e.g., a heater 112) in thermal contact with a droplet, plug, slug, or continuous flow of the reagents including one or more amplicons (e.g., while the reagents are in a microfluidic channel 102 corresponding with the heater 112) and measuring the resistance of the thermal control element (e.g., measuring the resistance of the heater 112) at temperatures that coincide with two or more features (e.g., melting points) of the thermal response profile of the amplicons.

In other embodiments, the calibration equation may model the relation between other electrical factors, such as the current, electric potential, applied power, resistivity, conductivity, or other related quantities. In some aspects, the measurement value may be an independently controlled aspect of the thermal control element that is related to the temperature of the thermal control element. In other aspects, the measurement value could be any factor related to the temperature of the thermal control element.

In some embodiments, the calibration equation may contain more coefficients to be determined. For example, in the case where the measurement value is resistance, some calibration equations can model a quadratic relationship as shown in Equation 2:

$$T = k_0 + k_1 R + k_2 R^2 \quad \text{Equation 2}$$

In this case, an amplification product resulting from reagents having three or more features in its thermal response profile may be preferable to more accurately determine all of the coefficients. Further, one of ordinary skill will comprehend that this approach may be expanded for a compound calibrator having n or more features, using Equation 3:

$$T = k_0 + k_1 R + k_2 R^2 + \ldots k_{n-1} R^{n-1} \quad \text{Equation 3}$$

Furthermore, in some embodiments, more accurate values for the coefficients may be obtained by utilizing reagents having more features than there are coefficients to be determined (i.e., determine more correspondences between temperature and resistance of the thermal control element than there are coefficients). The resulting over-determined system can be solved, for example, using the least squares method.

In some embodiments, the thermal control element can be calibrated using an ambient temperature (i.e., room temperature) in addition to one or more temperatures determined based on features (e.g., melting points) of thermal response profiles. For example, calibration of the temperature of the microfluidic channel may include determining the thermal control element's output (e.g., the resistance of the heater 112) while the thermal control element is at a known, ambient temperature. In some embodiments, the ambient temperature can be measured with a separate temperature measurement device such as, for example, a precision RTD or thermocouple. However, any other suitable temperature measurement device including non-contact methods are appropriate as will be understood by those skilled in the art.

In other embodiments, the one or more amplicons used to calibrate temperature in a microfluidic channel of a microfluidic device may be synthetic amplicons, i.e. amplicons produced from synthetic sequences. In a preferred embodiment, the amplicon(s) derived from synthetic sequences will not interfere with clinical samples and may be produced from a vector. In a preferred embodiment, the one or more calibrants are designed from a synthetic sequence will not interfere with clinical samples and may easily be produced from a vector. In some embodiments, the one or more sequences are chosen such that they are not present in human genomic DNA. In other embodiments, the one or more sequences are chosen such that they are not present in mammalian genomic DNA. In additional embodiments, the one or more sequences are chosen such that they are not present in vertebrate DNA. In one embodiment, one of the one or more amplicons is named RFCAL-100. In another embodiment, one of the one or more amplicons is named RFCAL-200. In certain embodiments, the one or more amplicons are cloned in a vector. Any suitable vector well known to the skilled artisan may be used, such as a plasmid, a virus, and the like, into which a synthetic sequence has been inserted.

In some embodiments of the present invention, one or more of the one or more amplicons used to calibrate temperature in a microfluidic channel of a microfluidic device may be produced from UCEs. UCEs are involved in transcription regulation and in early development, and scientists believe UCEs were functional introns common to all life forms in the evolutionary time. In the human genome, there are a large number of UCEs, which may be sequences longer than 200 base pairs (bp). UCEs are also conserved among vertebrates' genomes as well. UCEs are present in all human chromosomes, except for Y and 21 chromosomes. UCEs have a very low mutation rate and have not changed at all during the last 300 millions years or more.

Aspects of the present invention can be used to calibrate resistive sensors, thermistors, diode temperature sensors, thermocouples, or any other suitable temperature measuring devices. The present invention can further be used to calibrate resistive sensors that are also used for heating, such as thin-film platinum elements (or nickel or copper or any other material as would be understood by those skilled in the art).

Another aspect of the present invention is, for temperature shifts in space and/or time that follow an observable pattern or trend, the application of a temperature correction to regenerate and/or replot temperature corrected melt curves and decrease the variance in melting temperatures. In other words, aspects of the present invention may recalibrate the temperature profile such that the measured temperatures are closer to their true values. Accordingly, aspects of the present invention may be used to decrease the misclassification rate when genotyping. In some embodiments, neighboring positive control DNA samples (in space or time) of known melting temperatures may be used to calculate and apply a temperature correction to DNA melt curves of unknown genotypes. In some embodiments, positive control samples (i.e., calibrants or amplicons having a known or expected melt temperature) may be melted before and/or after and/or simultaneously with unknown samples, and the derivative of their melt curves may exhibit one or two or more peaks.

Figure 19A:
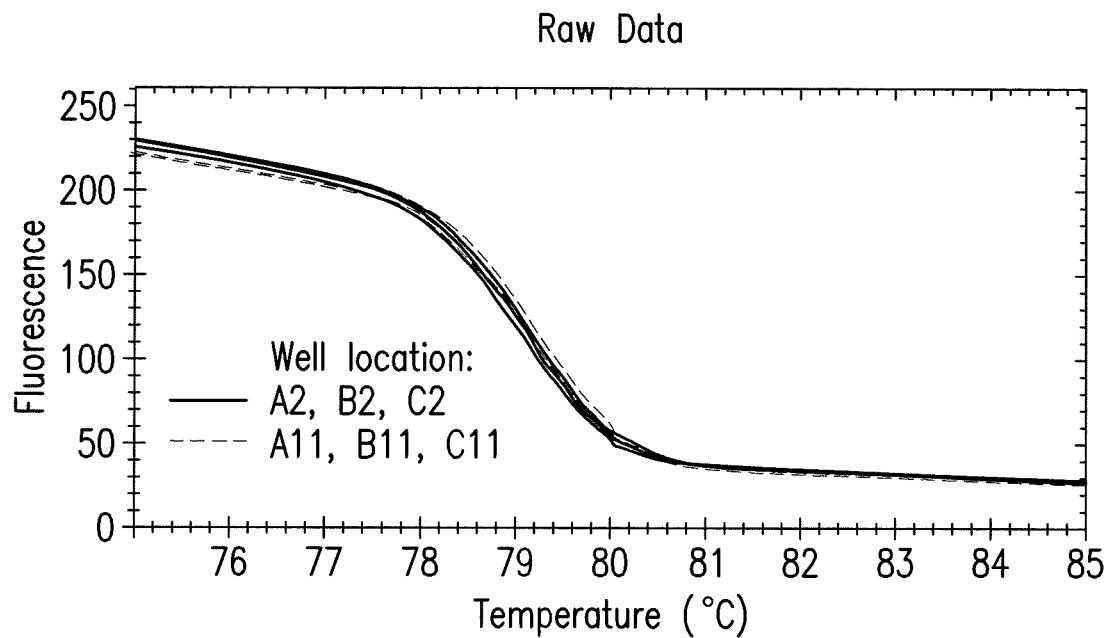
FIG. 19A illustrates fluorescence versus temperature melt curves for a calibrant according to an embodiment of the invention on a well plate based system.
Figure 19B:
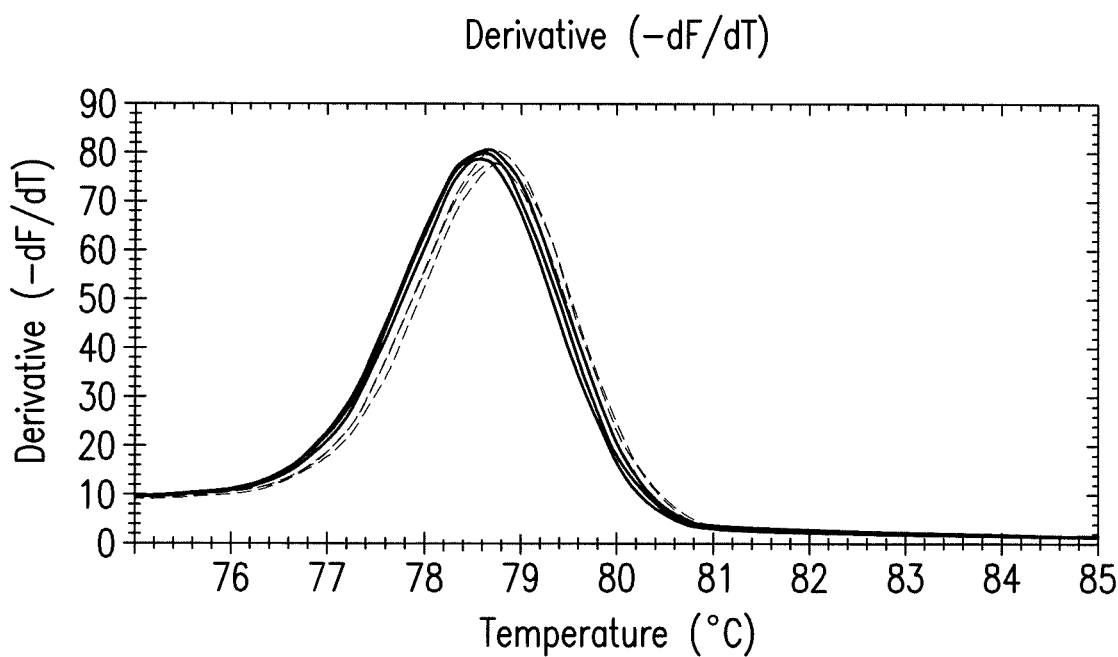
FIG. 19B illustrates that the derivative of fluorescence with respect to temperature melt curves for the UCE calibrant exhibits a single peak.
Figure 20A:
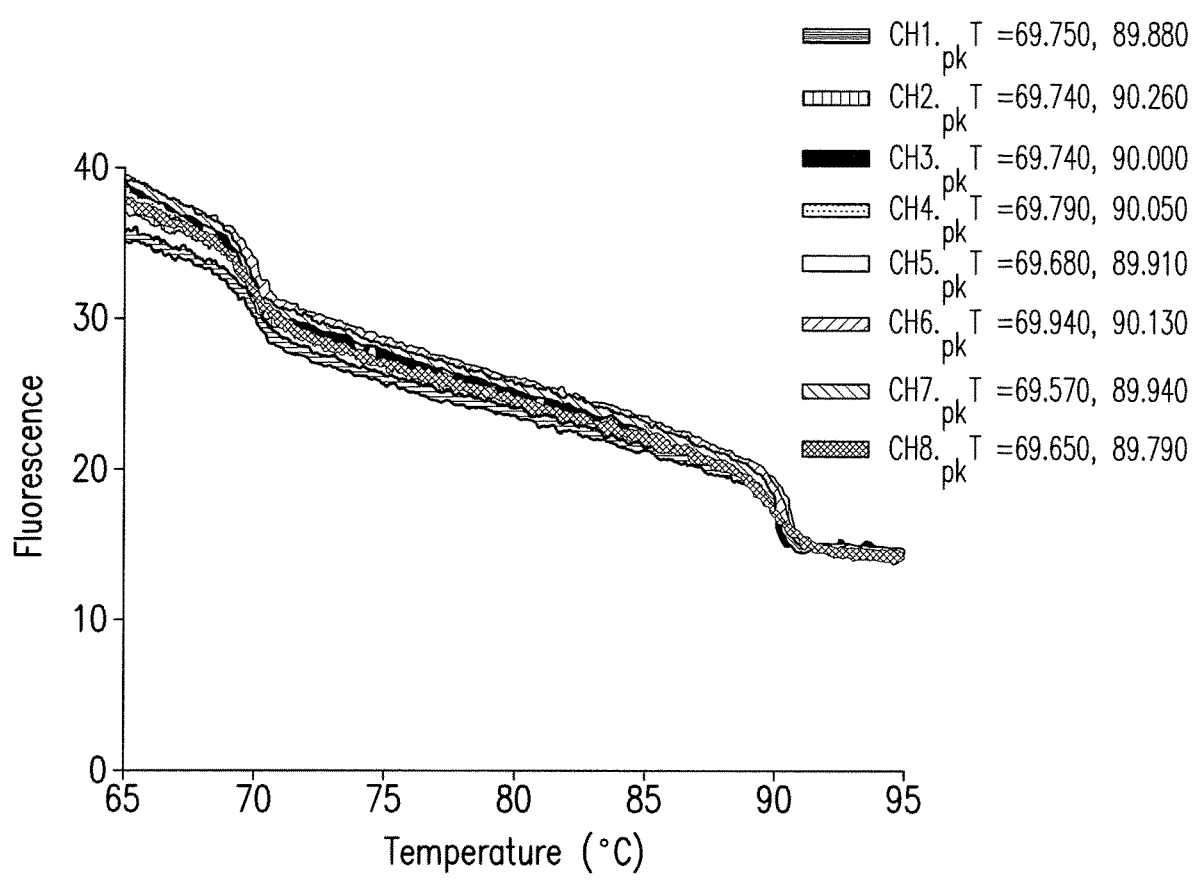
FIG. 20A illustrates fluorescence versus temperature melt curves for a calibrant according to an embodiment of the invention on a microfluidic channel based system.
Figure 20B:
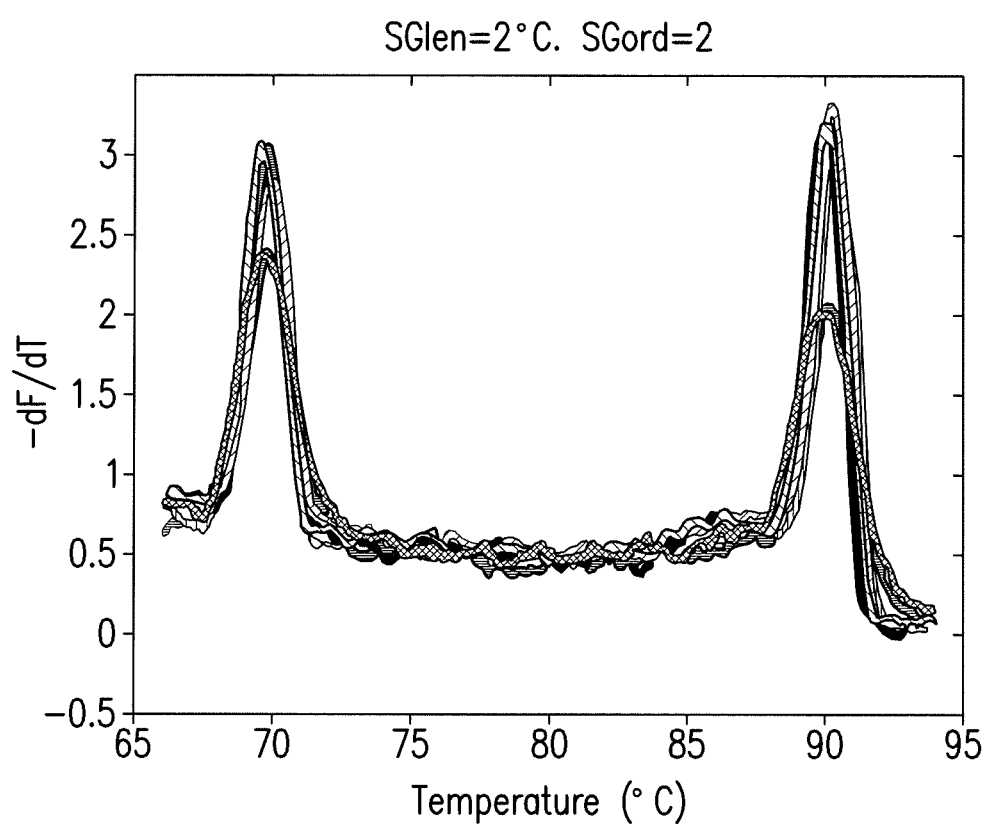
FIG. 20B illustrates that the derivative of fluorescence with respect to temperature melt curves for the calibrant exhibits two peaks.

For example, FIG. 19A illustrates fluorescence versus temperature melt curves for a calibrant (e.g., a 207 bp UCE sequence described in more detail below) according to an embodiment of the invention on a well plate based system, and FIG. 19B illustrates that the derivative of fluorescence with respect to temperature melt curves for the UCE calibrant exhibits a single peak. For another example, FIG. 20A illustrates fluorescence versus temperature melt curves for a calibrant (e.g., a synthetic calibrant comprising RFCAL-100 and RFCAL-200 described in more detail below) according to another embodiment of the invention on a microfluidic channel based system, and FIG. 20B illustrates that the derivative of fluorescence with respect to temperature melt curves for the calibrant exhibits two peaks (i.e., one peak around 70° C. and a second peak around 90° C.). Aspects of the present invention may use a calibrant producing a melt curve having a derivate that exhibits one or two peaks, such as those shown in FIGS. 19B and 20B, to calibrate and apply a temperature correction to DNA melt curves of unknown genotypes.

One aspect of the present invention is a method of calibrating the temperature of a thermal melt in a microfluidic channel present in a microfluidic system. The method may comprise: (a) introducing into the microfluidic channel reagents comprising a test sample containing human genomic DNA, at least a pair of primers for one or more nucleic acids of interest and a pair of primers for a calibrant, wherein the calibrant is found in genomic DNA; (b) amplifying the genomic DNA to produce a calibrant amplicon and an amplicon of the at least one nucleic acid of interest; (c) melting the amplicons and determining a melting temperature of each of the amplicons; (d) comparing the determined melting temperature of the calibrant amplicon with an expected melting temperature of the calibrant amplicon; and (e) calibrating the melting temperature of the amplicon of the at least one nucleic acid of interest based on the melting temperature of the calibrant amplicon.

Figure 3B:
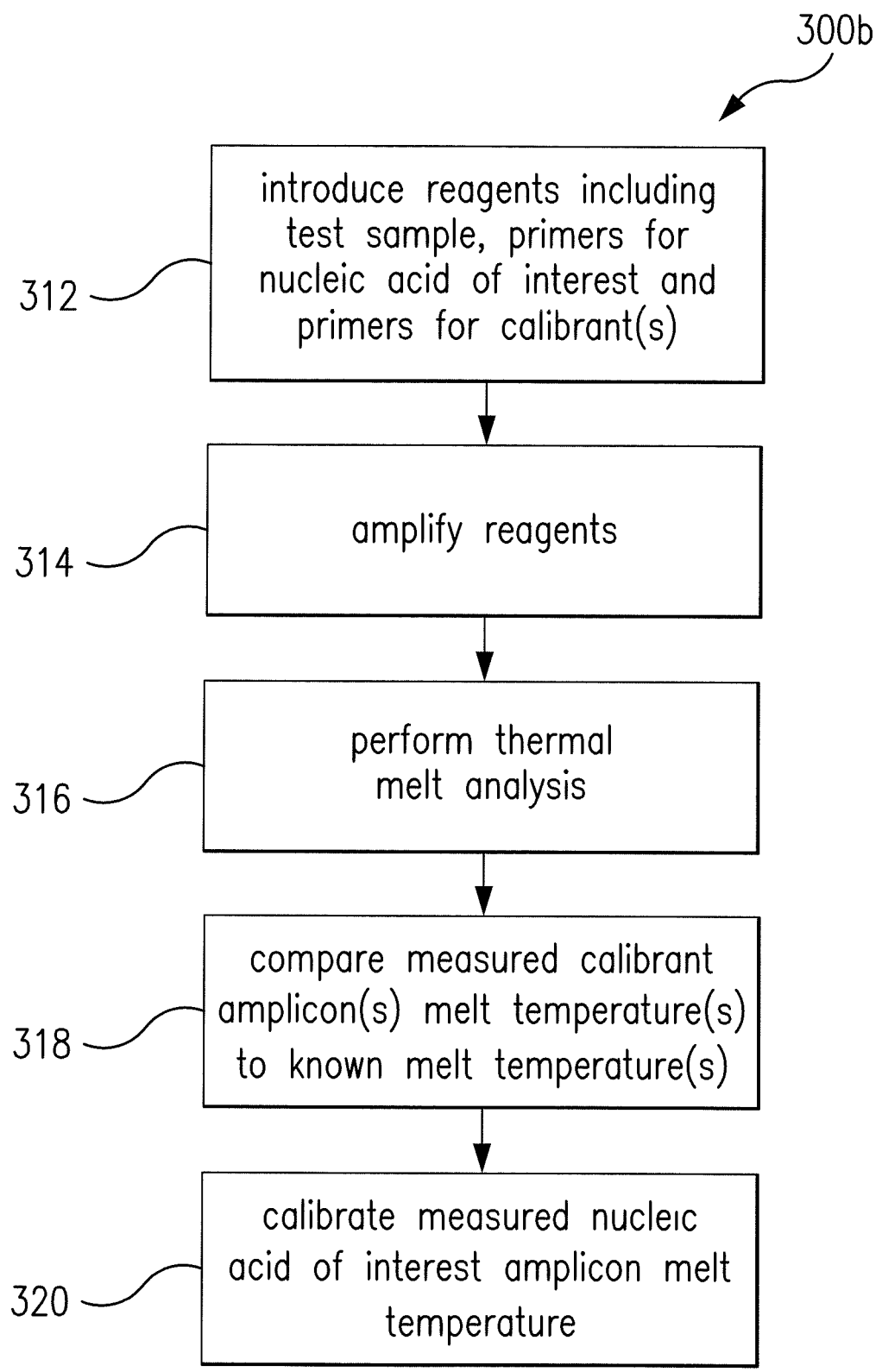
FIG. 3B is a flow chart illustrating a process for calibrating the temperature of a thermal melt in a microfluidic channel present in a microfluidic system in accordance with an embodiment of the present invention.

FIG. 3B illustrates a process 300*b* for calibrating the temperature of a thermal melt in a microfluidic channel of a microfluidic device in accordance with an embodiment of the present invention. The process 300 may begin at step 312 at which reagents are introduced into the microfluidic channel. The reagents may include a test sample, a pair of primers for a nucleic acid of interest and/or a pair of primers for a calibrant. In some embodiments, the reagents may also include one or more additional pairs of primers for one or more additional nucleic acids of interest. In one embodiment, the test sample may contain human genomic DNA. However, the test sample may contain other types of DNA in addition to or as an alternative to human genomic DNA. In some embodiments, the calibrant is found in genomic DNA, such as, for example, human genomic DNA. In one non-limiting embodiment, the calibrant is a UCE. However, in other embodiments, the calibrant may be a synthetic calibrant. In some embodiments, such as embodiments where the calibrant is a UCE, the calibrant may be included in the test sample. In other embodiments, such as embodiments where the calibrant is synthetic, the reagents additionally include the calibrant. In some embodiments, the reagents may include one or more additional pairs of primers for one or more additional calibrants, which may also be included in the reagents. In a preferred embodiment, each one of the one or more calibrants has a known thermal melting temperature. In other words, in a preferred embodiment, the temperature at which each of the one or more amplicons is expected to melt is known. Step 312 may include the reagents being introduced in separate fluid segments, such that the primers for the nucleic acids of interest may be in a separate fluid segment than the primers for the calibrant. A fluid segment containing the primers for the calibrant may be introduced before and after multiple fluid segments containing primers for the nucleic acid of interest, or the fluid segment containing the primers for the calibrant may be alternately introduced with fluid segments containing the primers for the nucleic acids of interest, such that a fluid segment containing the primers for the calibrant may be present before and after each fluid segment containing primers for the nucleic acids of interest.

At step 314, the reagents, which may include the test sample, at least a pair of primers for one or more nucleic acids of interest and at least of pair of primers for one or more calibrants are amplified. Amplification of the reagents in step 314 may produce an amplification product comprising one or more calibrant amplicons and an amplicon of the one or more nucleic acids of interest. In one embodiment, the amplification may be performed by exposing the reagents to a PCR temperature cycle a plurality of times to effect PCR amplification. The reagents may be exposed to the PCR temperature cycle in a PCR zone of a microfluidic device (e.g., PCR zone 104 of microfluidic device 100). However, any known method and/or device for application of reagents may be used.

At step 316, a thermal melt analysis may be performed on the amplification product. In other words, the one or more calibrant amplicons and an amplicon of the one or more nucleic acids of interest may be melted, and the temperature at which the amplicons melt may be measured. In this way, the process 300b may determine the temperature at which each of the amplicons in the amplification product in a microfluidic channel melted. In one embodiment, the thermal melt analysis may be performed by exposing the amplicons to a temperature ramp. The amplicons may be exposed to the temperature ramp (e.g., heating the thermal control element at, for example, 0.5 degrees Celsius per second over a range of temperatures that includes temperatures corresponding to the features of the thermal response profiles of the amplicons) in a thermal melt zone of a microfluidic device (e.g., thermal melt zone 106 of microfluidic device 100). During the thermal ramp, a dependent variable (e.g., fluorescence intensity) of the amplicons and the measurement value of the thermal control element is monitored to generate a thermal response profile. The temperature may be measured by a thermal melt zone fluorescence measurement system (e.g., thermal melt zone fluorescence measurement system 232). However, any known method and/or device for performing thermal melt analysis may be used.

In one embodiment, thermal melt analysis may be an analysis of a dependent variable related to a solution (e.g., reagent solution) that is subject to a thermal variation, i.e., the relationship between a solution's temperature and the dependent variable. In some embodiments, the thermal response profile may be a melt curve, i.e. the fluorescent melt analysis of a solution to determine the relationship between the amount of fluorescence and the solution's temperature. In some embodiments, generating such a thermal response profile can include loading a microfluidic chip (e.g., the microfluidic chip 100) into a system for controlling reactions in the microfluidic chip (e.g., system 200), loading a droplet, plug, slug, or continuous flow of the reagents including the one or more amplicons into the chip (e.g., into a microfluidic channel 102), and controlling a thermal control element (e.g., heater 112) that is in thermal communication with the amplicons to heat the amplicons while monitoring the temperature of the thermal control element and while monitoring the dependent variable (e.g., fluorescence in the case in which a melt curve is obtained) of the amplification product.

In one embodiment, the apparent (i.e., measured) temperatures of each feature (e.g., the apparent melt temperature corresponding to each of the one or more calibrant amplicons and/or each of the amplicon of the one or more nucleic acids of interest) may be identified from a thermal response profile. In some embodiments, the apparent temperatures may be determined from the derivative plot using peak-picking. In other embodiments, the apparent temperatures may be determined by cross-correlating the derivative plot with a known template (i.e., an expected thermal response profile) for each amplicon, or shifting and stretching the thermal response profile to match a predefined template.

At step 318, for each of the one or more calibrant amplicons, the measured temperature at which the calibrant amplicon melted is compared to the known (i.e., expected) thermal melt temperature for the calibrant amplicon. The comparison may be performed by, for example, a digital or analog comparator. The comparator may be part of a control system of a microfluidic system (e.g., control system 250 of system 200). However, any known method and/or device for performing the comparison may be used.

At step 320, the melting temperature(s) of the amplicon of the one or more nucleic acids of interest of the microfluidic channel is calibrated based on the measured melt temperature(s) of the one or more calibrant amplicons. For example, the melting temperature(s) of the amplicon of the one or more nucleic acids of interest of the microfluidic channel is calibrated based on the results of the comparison(s) of the measured melt temperature(s) of the one or more calibrant amplicons to the respective known thermal melt temperature(s). In one non-limiting embodiment, the calibration is performed by shifting the melt temperature(s) of the amplicon of the one or more nucleic acids of interest in accordance with the results of the comparison(s) of the measured melt temperature(s) of the one or more calibrant amplicons to the respective known thermal melt temperature(s).

As noted above, in some embodiments, the microfluidic channel reagents include a pair of primers for one nucleic acid of interest. As used herein, nucleic acid of interest refers to a nucleic acid whose presence or absence is to be determined in a test sample. In other embodiments, the microfluidic channel reagents include a pair of primers for each of two or more nucleic acids of interest. In some embodiments, the calibrant found in genomic DNA is a DNA segment that is known to be present in all genomic DNA of interest, such as human genomic DNA. In other embodiments, the calibrant is a UCE. In some embodiments, the microfluidic channel reagents may contain a pair of primers for the calibrant. In certain embodiments, the amplification of the microfluidic reagents produce a calibrant amplicon. In certain embodiments, the amplification of the calibrant does not affect amplification of the one or more nucleic acids of interest.

In some embodiments, the determining the melting temperature of each of the amplicons may comprise: obtaining a derivative of a melt curve of the melting of the amplicons using a Savitzky-Golay filter, and finding the temperatures at the maximum negative derivatives of the derivative of the melt curve. The determining the melting temperature of each of the amplicons may comprise: cross-correlating peaks of a derivative of a reference melt curve against peaks of a derivative of a melt curve of the melting of the amplicons, and selecting the temperatures having the highest correlation as the melting temperatures of the amplicons. The comparing the determined melting temperature of the calibrant amplicon with the respective expected melting temperature of the calibrant amplicon may comprise calculating a slope correction factor and an intercept correction factor using the respective expected melting temperature of the calibrant amplicon. Calibrating the melting temperature of each of the amplicons of the nucleic acids of interest may comprise calculating an adjusted temperature using the calculated slope correction factor and the calculated intercept correction factor of the calibrant amplicon.

The method may comprise using the comparison of the determined melting temperature of the calibrant amplicon with the respective expected melting temperature of the calibrant amplicon to validate amplification of the one or more amplicons of the one or more nucleic acids of interest. The validation may comprise determining the corrected melting temperatures of the amplicons of the nucleic acids of interest.

In one embodiment, thermal melt analysis may be an analysis of a dependent variable related to a solution (e.g., reagent solution) that is subject to a thermal variation, i.e., the relationship between a solution's temperature and the dependent variable. In some embodiments, the thermal response profile may be a melt curve, i.e. the fluorescent melt analysis of a solution to determine the relationship between the amount of fluorescence and the solution's temperature. In some embodiments, generating such a thermal response profile can include loading a microfluidic chip (e.g., the microfluidic chip 100) into a system for controlling reactions in the microfluidic chip (e.g., system 200), loading a droplet, plug, slug, or continuous flow of the reagents including test sample and primers into the chip (e.g., into a microfluidic channel 102) amplifying the calibrant and nucleic acid of interest, and controlling a thermal control element (e.g., heater 112) that is in thermal communication with the amplification product to heat the amplification product while monitoring the temperature of the thermal control element and while monitoring the dependent variable (e.g., fluorescence in the case in which a melt curve is obtained) of the amplification product.

In one embodiment, the apparent (i.e., measured) temperatures of each feature (e.g., the apparent melt temperature corresponding to each amplicon) may be identified from a thermal response profile. In some embodiments, the apparent temperatures may be determined from the derivative plot using peak-picking. In other embodiments, the apparent temperatures may be determined by cross-correlating the derivative plot with a known template (i.e., an expected thermal response profile) for each calibrant, or shifting and stretching the thermal response profile to match a predefined template.

In some embodiments of the present invention, one or more of the one or more calibrants used to calibrate temperature of a thermal melt in a microfluidic channel of a microfluidic device may be UCEs. Because UCEs are present in all genomic DNA, every time that an amplification is done using a genomic DNA, one or more specific Ultra Conserved Element (UCE) DNA sequences may also be amplified.

In some embodiments of the present invention, a pair of primers may be designed to amplify a specific UCE sequence that is used as a calibrant. Using an amplification process, such as PCR, the pair of primers may be used to make the same UCE amplicon over and over. The UCE amplicon is will always shows the same melt temperature ($T_M$). Based on the characteristic of the UCE amplicons always showing the same $T_M$, the UCE amplicon can be used, for example, for calibrating melting temperature in a microfluidic system having one or more microfluidic channels.

Accordingly, in one aspect, the present invention provides methods, devices, and systems for using a pair of primers for amplifying a calibrant found in human genomic DNA in PCR and thermal melt analysis devices such that the calibrant amplicon is used to calibrate the melting temperature of an amplicon of a nucleic acid of interest. In one embodiment, the UCE primers are used at the same time with at least a pair of primers for one or more nucleic acids of interest, during PCR amplification and melting, the melt temperature ($T_M$) of an amplicon generated from a nucleic acid of interest is correct. This may be accomplished because the UCE primer product may have a known $T_M$.

Embodiments of the present invention can be used in a variety of instruments but are particularly useful in PCR and thermal melt systems that perform in vitro diagnostics. Embodiments of the present invention may be used to calibrate sensors and heaters that are intended for thermal melt of samples (diagnostics) as well as other heaters and sensors within the instrument that perform entirely different functions (e.g., sample prep or PCR).

In another aspect, the present invention provides a multiple amplicon calibrator system. In other words, reagents containing two or more amplicons may be used to calibrate the temperature of a microfluidic channel. For instance, a dual amplicon calibrator may be used to generate accurate high resolution melting on certain microfluidic chip based systems. In a non-limiting embodiment, one or more of the multiple amplicons in the multiple amplicon calibrator system are Ultra Conserved Elements (UCEs). In another non-limiting embodiment, one or more of the multiple amplicons in the multiple amplicon calibrator system are synthetic. In another non-limiting embodiment, one or more of the multiple amplicons are UCEs, and one or more of the multiple amplicons are synthetic.

As described above, one embodiment of the present invention may utilize two amplicons. In one non-limiting example, one amplicon may be from a desired DNA sequence, and the other amplicon may be a UCE amplicon. In one embodiment, the DNA sequence may be derived from the sequence of any human gene or other sequence. One example of a gene that could be used is a sickle cell gene. One example of a sequence for the sickle cell gene is a 444 bp fragment. In another embodiment, the UCE amplicon is a 415 bp UCE amplicon. The melt temperature Tm for the sickle sequence is approximately 84° C., and the melt temperature Tm for the UCE sequence is 74° C. In this non-limiting example, both amplicons were derived by amplifying human genomic DNA. However, it is not necessary that both amplicons in a dual amplicon calibrator system be derived by amplifying human genomic DNA.

In certain embodiments, certain limitations may exist with the dual calibrant system using the amplicon derived from the 444 bp fragment of the sickle gene and the 415 bp fragment of the UCE described above. First, the span covered by the two calibrators may not cover the full range of anticipated melt temperatures. Second, the amplicons were derived from genomic DNA and thus potentially could serve as a source of contamination for subsequent amplification reactions. Finally, manufacture of these calibrators may require amplification from human DNA, which was obtained from DNA banks, such as the Coriell DNA banks. Thus, these calibrators may not represent material that would be easy to manufacture or guarantee as a source.

Another aspect of the present invention is a dual amplicon calibrator system with a wide temperature span and two or more amplicons derived from synthetic sequences. In a preferred embodiment, the amplicons are designed from synthetic sequences so that they may be readily produced. In some embodiments, the sequences are chosen such that they are not present in human genomic DNA. In other embodiments, the sequences are chosen such that they are not present in mammalian genomic DNA. In additional embodiments, such sequences are chosen such that they are not present in vertebrate DNA. In some embodiments, the sequences are chosen to produce amplicons with a $T_M$ span greater than 5 degrees Celsius, preferably greater than 10 degrees Celsius, and more preferably greater than 20 degrees Celsius. In one embodiment, a first amplicon is named RFCAL-100. In another embodiment, a second amplicon is named RFCAL-200. In certain embodiments, the two or more amplicons are cloned in a vector. Any suitable vector well known to the skilled artisan may be used, such as a virus, and the like.

Non-Limiting Calibrant Examples

Genomic UCE Sequence

In a non-limiting example of a calibrant that may be used to calibrate the temperature of a microchannel of a microfluidic device is a UCE sequence with 207 base pairs. In development, the 207 bp UCE sequence was found using the Bioscience World web site www.biosciencworld.ca. The sequence was then checked against the National Center for Biotechnology Information (NCBI) Basic Local Alignment Search Tool (BLAST) database. The 207 bp sequence (SEQ ID NO:1) was shown to be part of the human chromosome 17 sequence (GenBank accession number AF287967.1). Using Primer 3 software, a set of two primers was designed (SEQ ID NO:2 and SEQ ID NO:3) which amplified a 71 bp product (SEQ ID NO:4).

Figure 4:
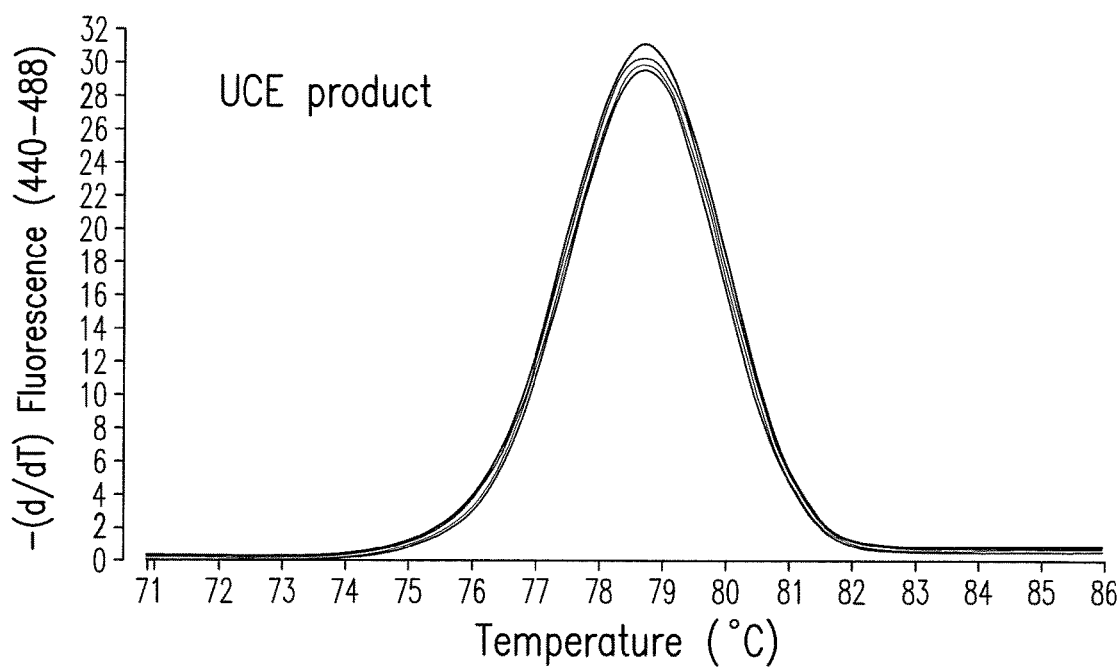
FIG. 4 illustrates thermal melt curves of an exemplary Ultra Conserved Element (UCE) calibrant in accordance with an embodiment of the invention on a microfluidic instrument showing three different genomic DNA.
Figure 5:
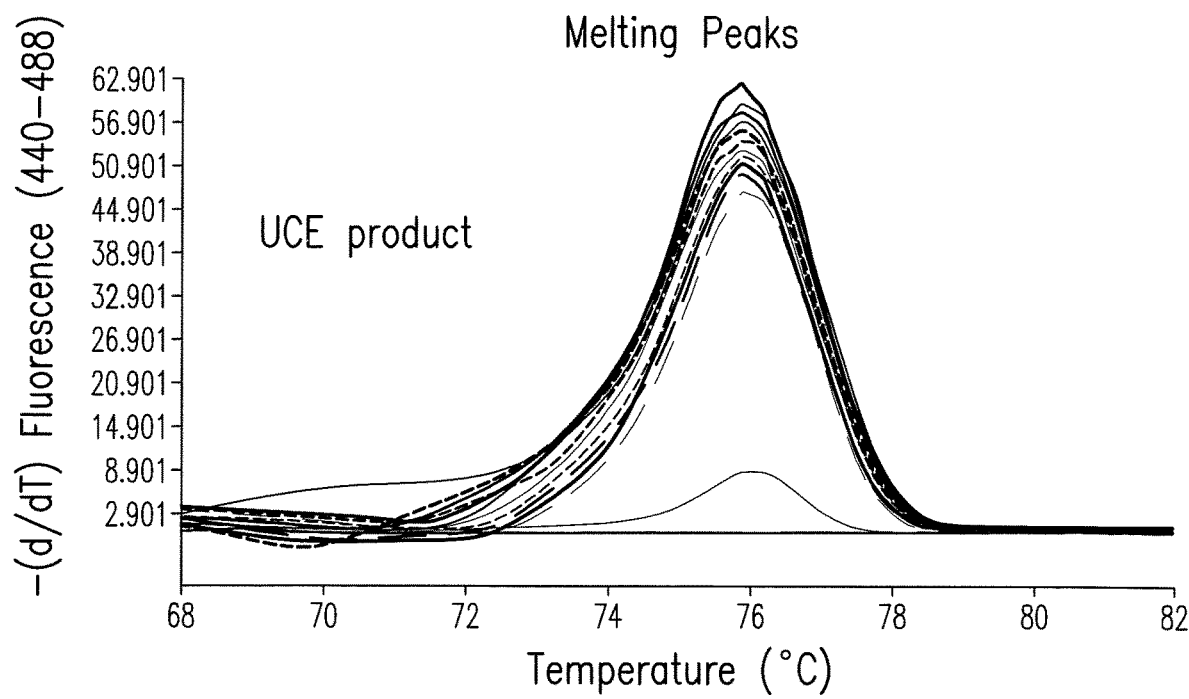
FIG. 5 illustrates thermal melt curves of an exemplary UCE calibrant in accordance with an embodiment of the invention on a Roche LightCycler® 480 (LC480) cycler platform showing seven different genomic DNA.

Experiments using the UCE primers and different genomic DNA samples showed that all samples were amplified, and all samples amplified show the same TMs. This experiment was done several times using the Roche Light-Cycler® 480 (LC480) cycler platform and a microfluidic instrument. The results of the experiments are shown in FIGS. 4 and 5. FIGS. 4 and 5 illustrate a so-called "derivative plot" which describes the derivative of fluorescence with respect to temperature as a function of temperature (e.g., dF/dT vs. T). FIG. 4 illustrates thermal melt curves of an amplification product generated using the UCE primers on the microfluidic instrument and shows three different genomic DNA. FIG. 5 illustrates thermal melt curves of an amplification product generated using the UCE primers on the LC480 cycler platform and shows seven different genomic DNA. The results of the experiments demonstrate that there were not variations on the melt temperatures $T_M$s. Thus, the experiments show that the UCE primers can be used to amplify UCE amplicons that act as temperature calibrators.

Figure 6:
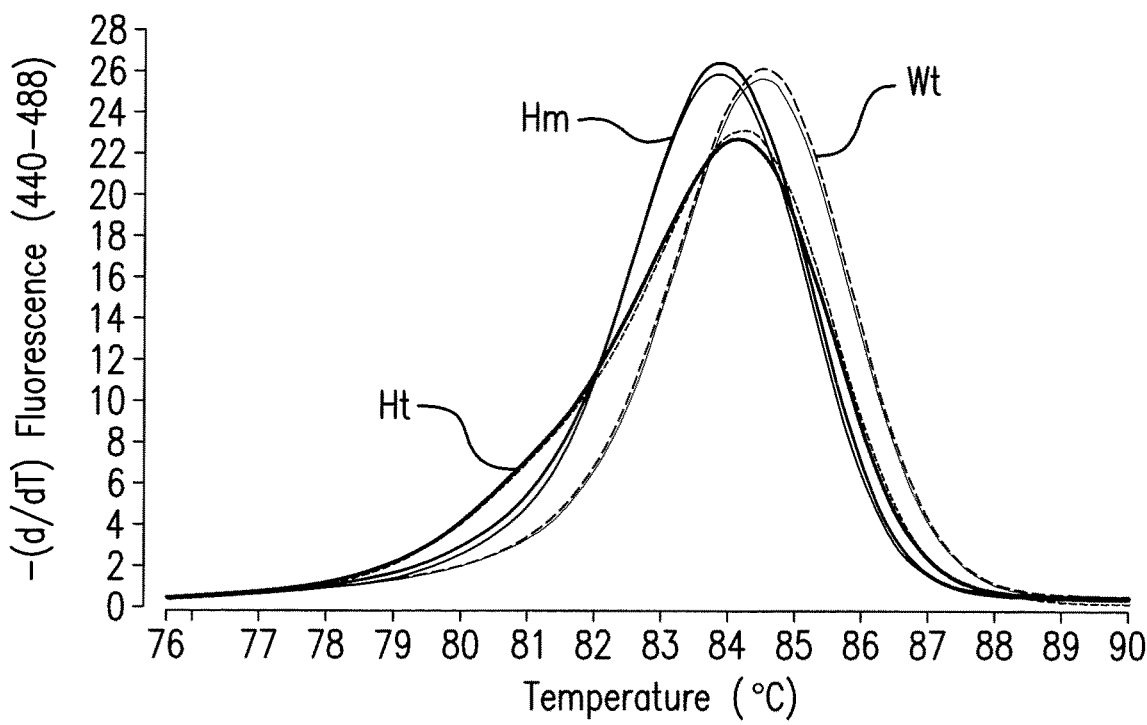
FIG. 6 illustrates thermal melt curves showing three different genotypes of a primer of study.
Figure 7:
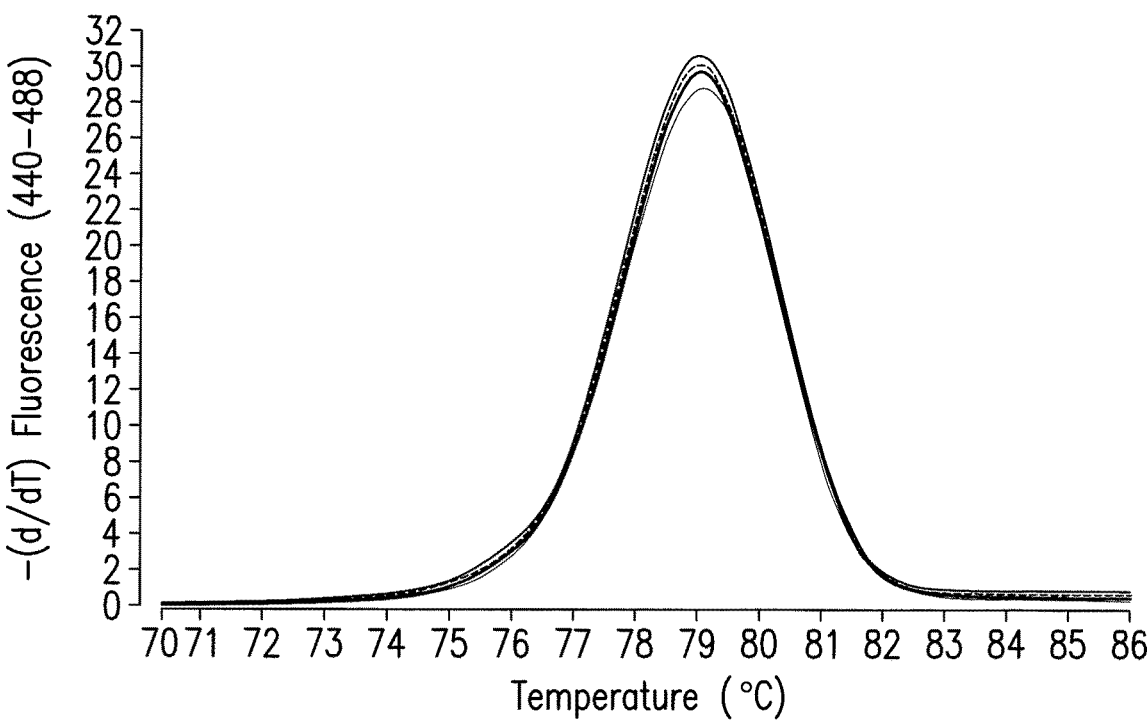
FIG. 7 illustrates thermal melt curves showing UCE products in accordance with an embodiment of the invention.

A second experiment was also performed. In the second experiment, a pair of primers for amplifying a nucleic acid of interest was loaded into the device and then subsequently the UCE primers were loaded into the device. The experiment was performed using a microfluidic instrument, and the results are shown in FIG. 6 and FIG. 7. FIG. 6 illustrates thermal melt curves showing three different genotypes of the primer of study (i.e., a wildtype genotype (Wt), a homozygous genotype (Hm), and a heterozygous genotype (Ht)). FIG. 7 illustrates thermal melt curves showing the UCE amplicon of the UCE primers.

Figure 8:
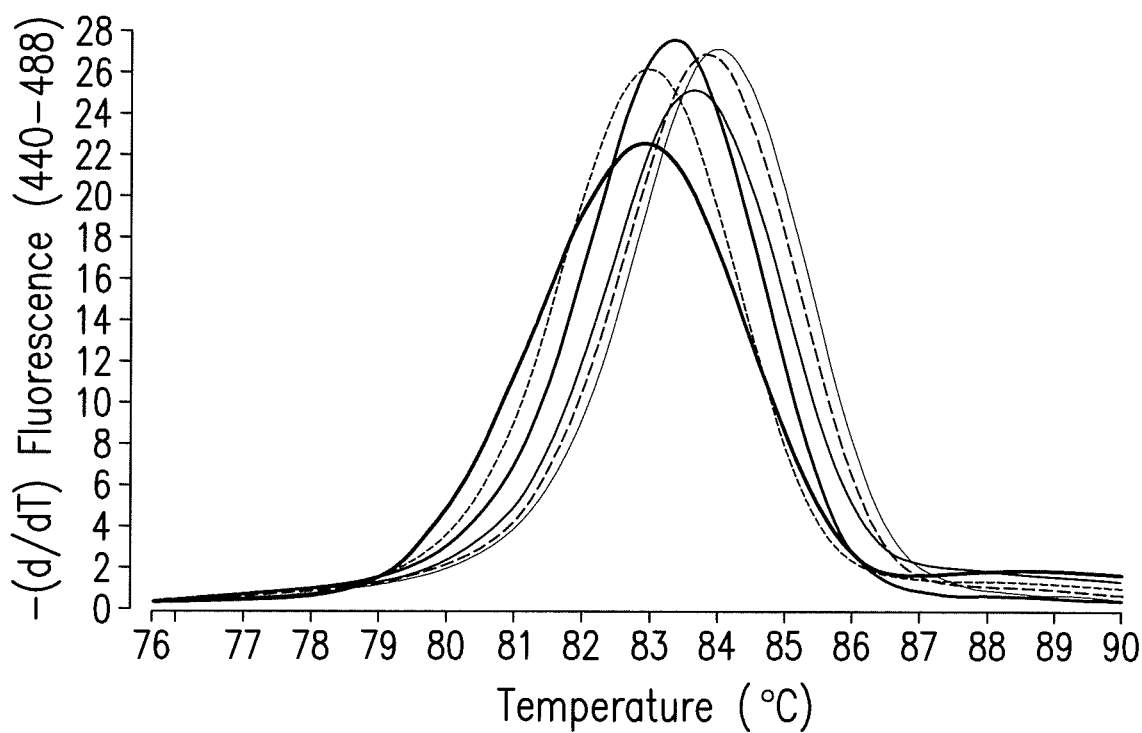
FIG. 8 illustrates a thermal melt curve showing three different genotypes.
Figure 9:
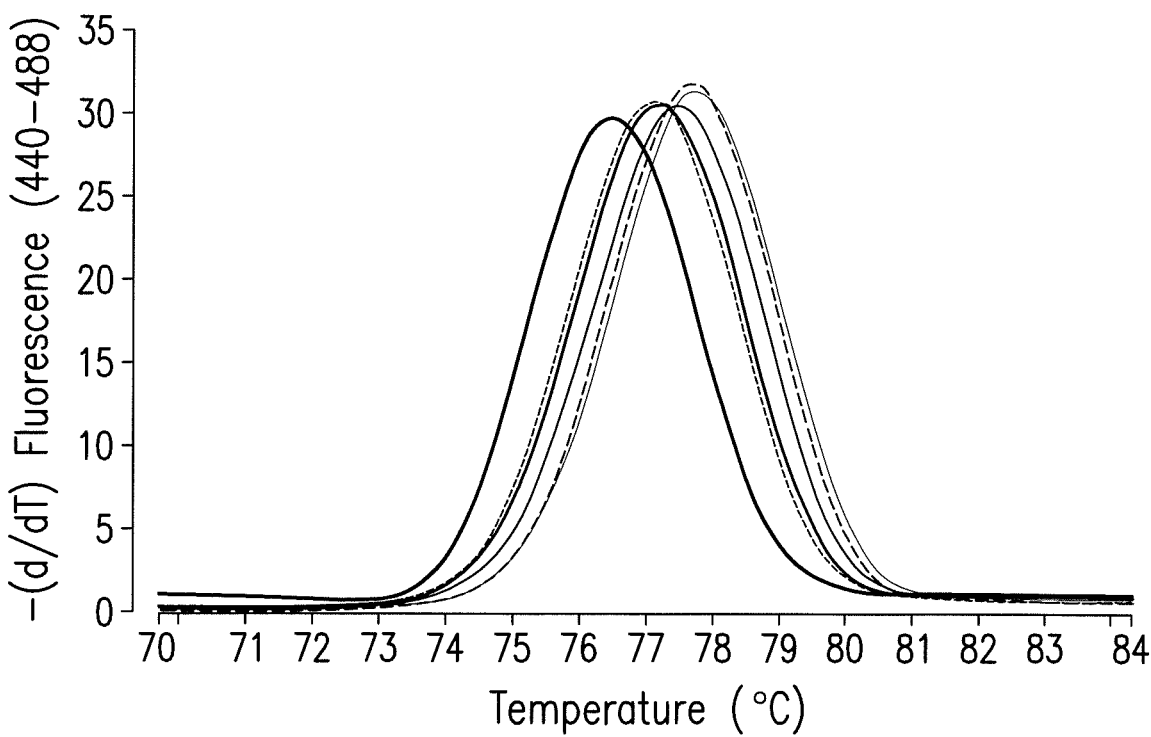
FIG. 9 illustrates a thermal melt curve showing a UCE amplification product in accordance with an embodiment of the invention.

In the event that the amplicon of the UCE primers show variations in melt temperatures $T_M$s, the amplification product of the primers of study also may also show variation on the melt temperatures $T_M$s. This may indicate an impossible genotype differentiation between DNA samples. An example of results indicating an impossible genotype differentiation between DNA samples are shown in FIG. 8 and FIG. 9. FIG. 8 illustrates a thermal melt curve showing three different genotypes, i.e. a wildtype genotype (Wt), a homozygous genotype (Hm), and a heterozygous genotype (Ht). FIG. 9 illustrates a thermal melt curve showing the UCE amplicon of the UCE primers. As illustrated in FIG. 9, the melt temperatures $T_M$s of the UCE amplicon of the UCE primers showed variation, and, as illustrated in FIG. 8, the melt temperatures of amplicon of the nucleic acid of interest showed the same variation.

Figure 10:
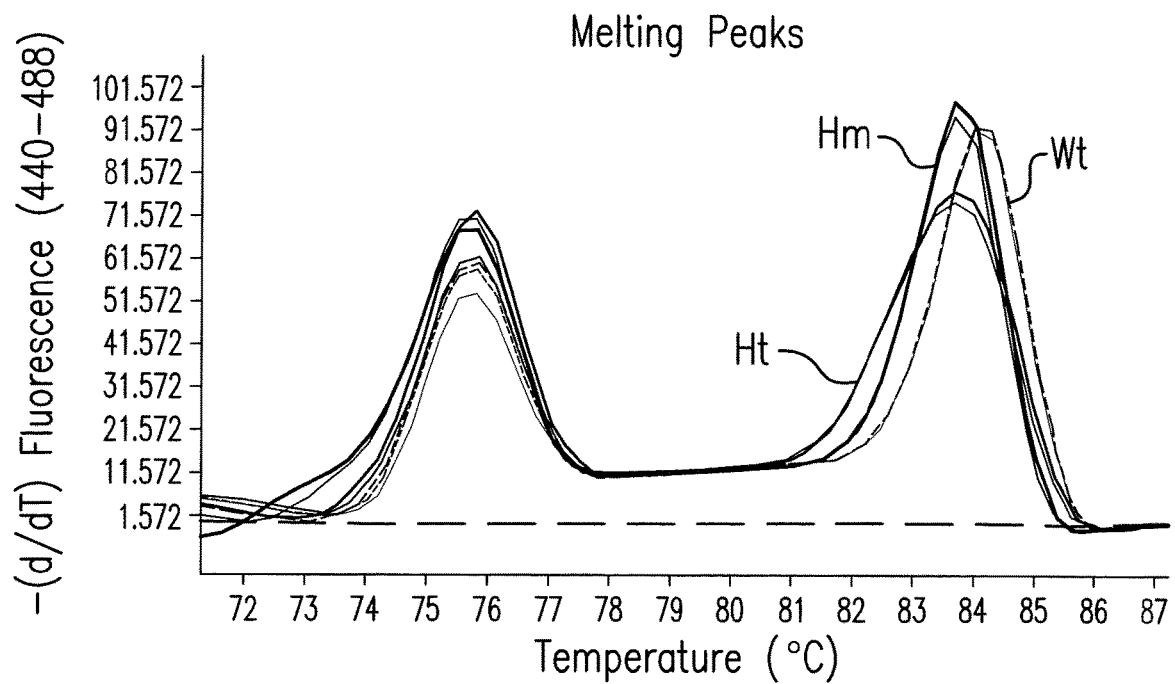
FIG. 10 illustrates a thermal melt curve showing an amplification product of a UCE primer and a primer of study in accordance with an embodiment of the invention.
Figure 11:
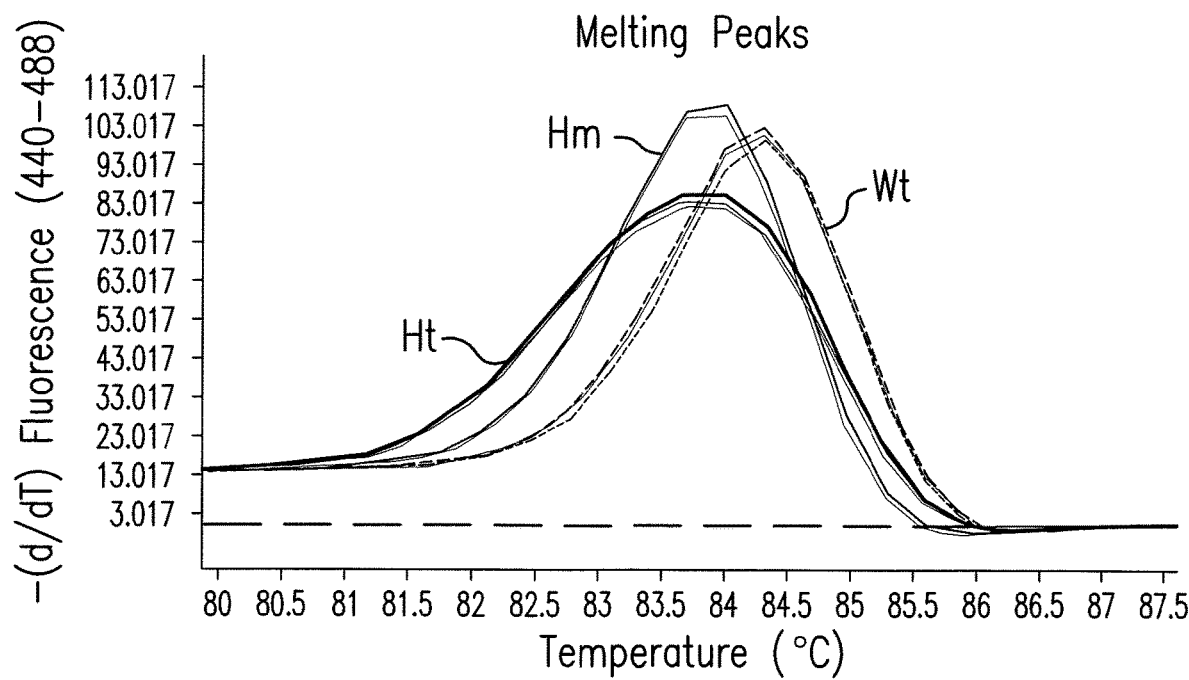
FIG. 11 illustrates a thermal melt curve showing the amplification product of the primer of study only.

To demonstrate that the UCE primers would not interfere with the amplification of a nucleic acid of interest and also help as a temperature calibrator, the following experiment was performed. The UCE primers and primers for a nucleic acid of interest were added together with the reaction mix components (i.e., reagents) and loaded into wells of a 96-well plate. PCR amplification and melting analysis were performed using a LC480 cycler platform. The results are shown in FIGS. 10 and 11. FIG. 10 illustrates a thermal melt curve showing the amplicon of the UCE primers added to the primers of study. FIG. 11 illustrates a thermal melt curve showing the amplicon of the nucleic acid of interest. The results illustrated in FIGS. 10 and 11 confirm that the UCE primers do not affect the amplification of the nucleic acid of interest. In other words, the same melt temperatures were obtained for the amplicon of the nucleic acid of interest regardless of whether the UCE primers were added with the primers of the nucleic acid of interest. The results also show that the UCE amplicon can be used as temperature calibrator.

As shown by the experiments discussed above, in some embodiments, two or more UCE primers may be used to provide a simple, fast and reliable procedure to check temperature inside a microfluidic channel in a microfluidic device or chip. Also, the experiments show that, in some embodiments, the two or more UCE primers may work as temperature calibrator when added following or ahead of the primers of study in a chip. In this case, the UCE amplicons may be used to determine whether the microfluidic channels temperature did or did not reach the ideal temperature set, and, therefore, may be used to validate a PCR run. The experiments further show that the two or more UCE primers works in the same fashion when used in a standard PCR instrument such as a LC480 cycler platform. In some embodiments, the UCE primers may be added with two or more primers of study and may not interfere with the amplification product of the primers of study.

In other embodiments, the UCE primers may function as a positive control to validate amplification has occurred. Obtaining a thermal response profile, for example, a melt curve, for the calibrant can serve as a positive control to demonstrate that no contamination of the reagents or other anomalies have occurred that would prevent amplification of the genomic DNA.

Synthetic Calibrator

In one non-limiting embodiment of one or more amplicons that may be used to calibrate the temperature of a microchannel of a microfluidic device, one or more of the one more amplicons may be synthetic amplicons. In an exemplary embodiment, the invention provides a dual amplicon calibrator system. The dual amplicon calibrator system may be used to improve calibrator performance and production. In one non-limiting example, the dual amplicon calibrator system may be used in a high resolution DNA melting instrument to improve calibrator performance and production. However, this is not required, and the dual amplicon calibrator system may be used in other systems. In some embodiments, the dual amplicon calibrator system may have individual calibrators designed for the dual system. In one embodiment, testing of the dual amplicon calibrator system was performed on a LC480 cycling platform, and non-limiting examples of possible formulations of the dual calibrator system were developed.

In one non-limiting example, two amplicons that may be used calibrate the temperature of a microfluidic channel in a microfluidic device are referred to herein as "sequence A" and "sequence B." Sequence A is 100 base pairs in length (SEQ ID NO:5), and sequence B is 200 base pairs in length (SEQ ID NO:6). Although a particular example is described, different sequences and sequences having different lengths may also be used in embodiments of the present invention.

In development of the non-limiting example of a dual calibrator in accordance with embodiments of the present, synthetic DNA constructs for the two calibration points were used to allow specific targeting of melting temperatures $T_M$s. Two DNA (i.e., sequence A and sequence B) sequences were created to work as a DNA template. The sequences were generated using a web-based program called "Random DNA Sequence Generator".

The two sequences were checked for similarity using BLAST program from NCBI. After no similarities were found with any sequence on the database, primers were targeted to the last 20 or 22 base pairs of the calibrator sequences. Primers for Sequence A are those set forth in SEQ ID NO:7 and DEQ ID NO:8. Primers or Sequence B are those set forth in SEQ ID NO:9 and SEQ ID NO:10. To check for primer specificity, the University of California, Santa Cruz, (UCSC) Genome Browser was used. The primers were verified to amplify only sequence A and sequence B.

Figure 12:
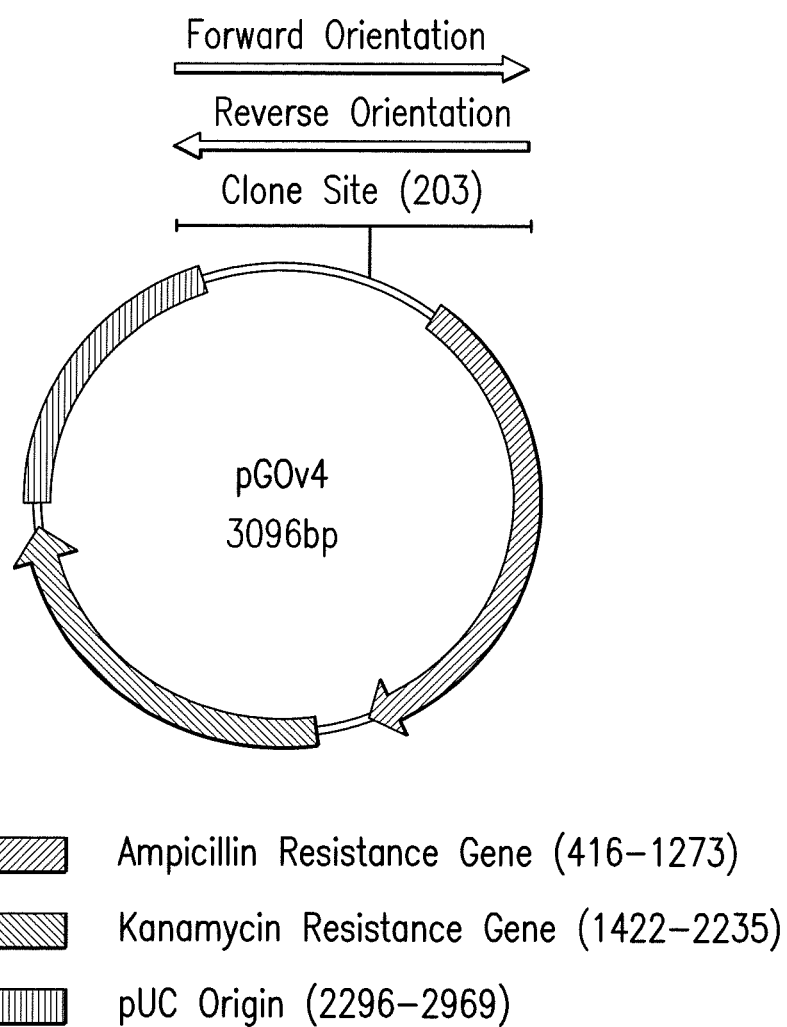
FIG. 12 illustrates a diagram depicting a pGOv4 vector map in relation to a synthetic sequence in accordance with an embodiment of the invention.

After this preliminary work was done, a sequence was constructed and ordered for both sequences using Gene Oracle clone services. Each construct was separately cloned into a pGOv4 vector. The pGOv4 vector is a pUC based vector which is Ampicillin and Kanamycin resistant. The pGOv4 map is shown in FIG. 12.

After the sequences were incorporated into a vector, the vectors were RFCAL-100 which contains Sequence A and RFCAL-200 which contains Sequence B. The sequence for RFCAL-100 is set forth in SEQ ID NO:11. The sequence for RFCAL-200 is set forth in SEQ ID NO:12.

All primers were ordered high-performance liquid chromatography (HPLC) purified at 200 nM from Invitrogen. However, primers of different purifications and/or from different providers may be used. The primers were then resuspended in PCR clean water at 100 uM. Genomic DNA was used as a control DNA. For example, VKORC1 wild type from Paragon Dx may be used as a control DNA. Tables below provide additional details regarding the reagents mixes and reagents catalog numbers.

TABLE 01

PCR reagents

| Reagent | Manufacture | Catalog # |
|---|---|---|
| Taq polymerase | Clontech Takara | RR006L |
| dNTPs | Fisher Scientific | AB-1124 |
| PCR water | Mo Bio | 17000-10 |
| MgCl2 | Ambion | AM9530G |
| LC Green Plus | Idaho Technology | BCHM-ASY-000 |
| 2x CULS Buffer | CULS | CULS0017 |
| Genomic DNA control | Paragon Dx | 004-GGCCGG |

The reagents described above were used in the following concentrations depicted on tables below to create a DNA Reagent Mix, a Taq Polymerase Reagent Mix and a Primer Reagent Mix.

TABLE 02

DNA mix
DNA Reagent Mix

| | Volume 1 Rx | Channel conc. | Stock conc. |
|---|---|---|---|
| DNA | 1.8 uL | 1 cp/nL | 50 ng/uL |
| 2x CULS Buffer | 7.5 uL | 1x | 2x |
| Alexa | 3 uL | 10 uM | 50 uM |
| Water | 2.69 uL | — | — |
| Total | 15 uL | — | — |

TABLE 03

CR mix
Taq Polymerase Reagent Mix

| | Volume 1 Rx | Channel conc. | Stock conc. |
|---|---|---|---|
| Enzyme | 3.3 uL | 0.25 U/uL | 5 U/uL |
| dNTPs | 1 uL | 0.37 mM | 25 mM |
| 2x CULS Buffer | 5 uL | 1x | 2X |
| Water | 0.7 uL | — | — |
| Total | 10 uL | — | — |

TABLE 04

Primer mix
Primer Reagent Mix

| | Volume 1 Rx | Channel conc. | Stock conc. |
|---|---|---|---|
| Forward primer | 0.4 uL | 1 uM | 100 uM |
| Reverse primer | 0.4 uL | 1 uM | 100 uM |
| 2x CULS Buffer | 5 uL | 1x | 2x |

TABLE 04-continued

Primer mix
Primer Reagent Mix

|  | Volume 1 Rx | Channel conc. | Stock conc. |
|---|---|---|---|
| MgCl2 | 0.1 uL | 3 mM | 1000 mM |
| LC Green Plus | 4 uL | 1x | 10x |
| Water | 0.1 uL | — | — |
| Total | 10 uL | — | — |

In this example, a total of 20 uL of a sum of all three reagent mixes were added in a well of a 96-well plate. Each primer was added in duplicate. The volume and percentage of each reagent mix is shown in the table below.

TABLE 05

Volume and proportion of reagents per well
Reagents per well

| Reagent Mix | Volume | Percentage |
|---|---|---|
| DNA | 12 uL | 60% |
| Polymerase | 3 uL | 15% |
| Primer | 5 uL | 25% |
| Total | 20 uL | 100% |

All three groups of reagents were ordered from the laboratory's in-house stock supply. DNA and primers were added subsequently on their respective mixes.

In this example, primers were added in duplicates. Positive control was added (e.g., VKORC1 primers plus control DNA (VKORC1)) as well as a Negative control (e.g., VKORC1 primers plus 2×CULS buffer).

Reactions were amplified on the Roche LC480 cycling platform. The PCR protocol used is shown on table below.

TABLE 07

PCR protocol
PCR Protocol

| Pre Amplification | 95° C./1 min | 1x |
|---|---|---|
| Amplification | 95° C./5 sec | 40x |
|  | 38° C./5 sec |  |
|  | 72° C./5 sec |  |
| Pos Amplification | 37° C./10 sec | 1x |
|  | 95° C./10 sec |  |
| Melt | 55° C.-95° C./15 sec | 1x |

Annealing temperature at 38° C. worked well for both primers set.

Figure 13:
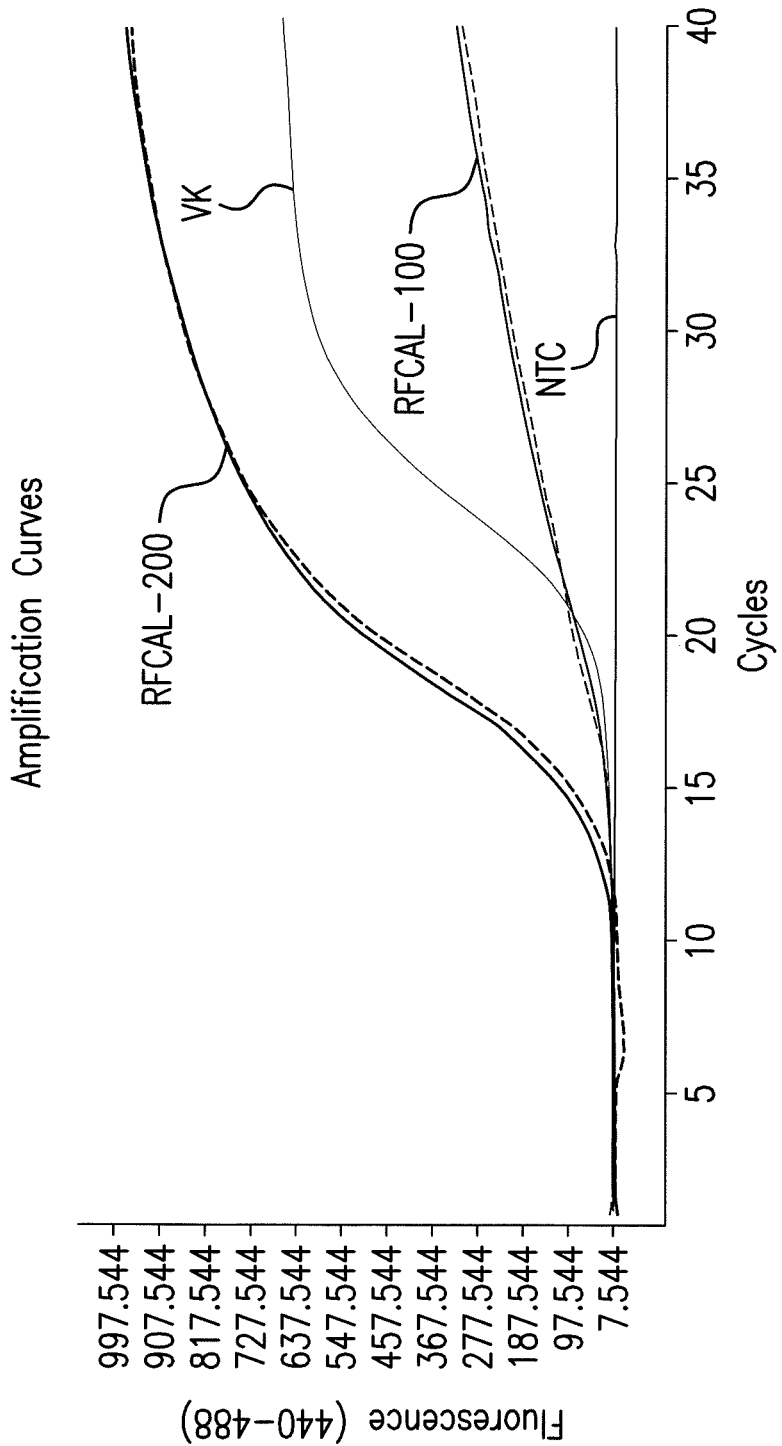
FIG. 13 illustrates a graph depicting the calibrators' product amplification on a LC480 cycler platform in accordance with an embodiment of the invention.

FIG. 13 illustrates a graph depicting the calibrators' product amplification on a LC480 cycler platform. As illustrated in FIG. 13, the samples were successfully amplified. RFCAL-200 DNA showed very strong fluorescent values. RFCAL-100 showed lower fluorescence values compared with RFCAL-200 as expected due to the sequence size and GC content. VKORC1 was used as a PCR positive control.

Figure 14:
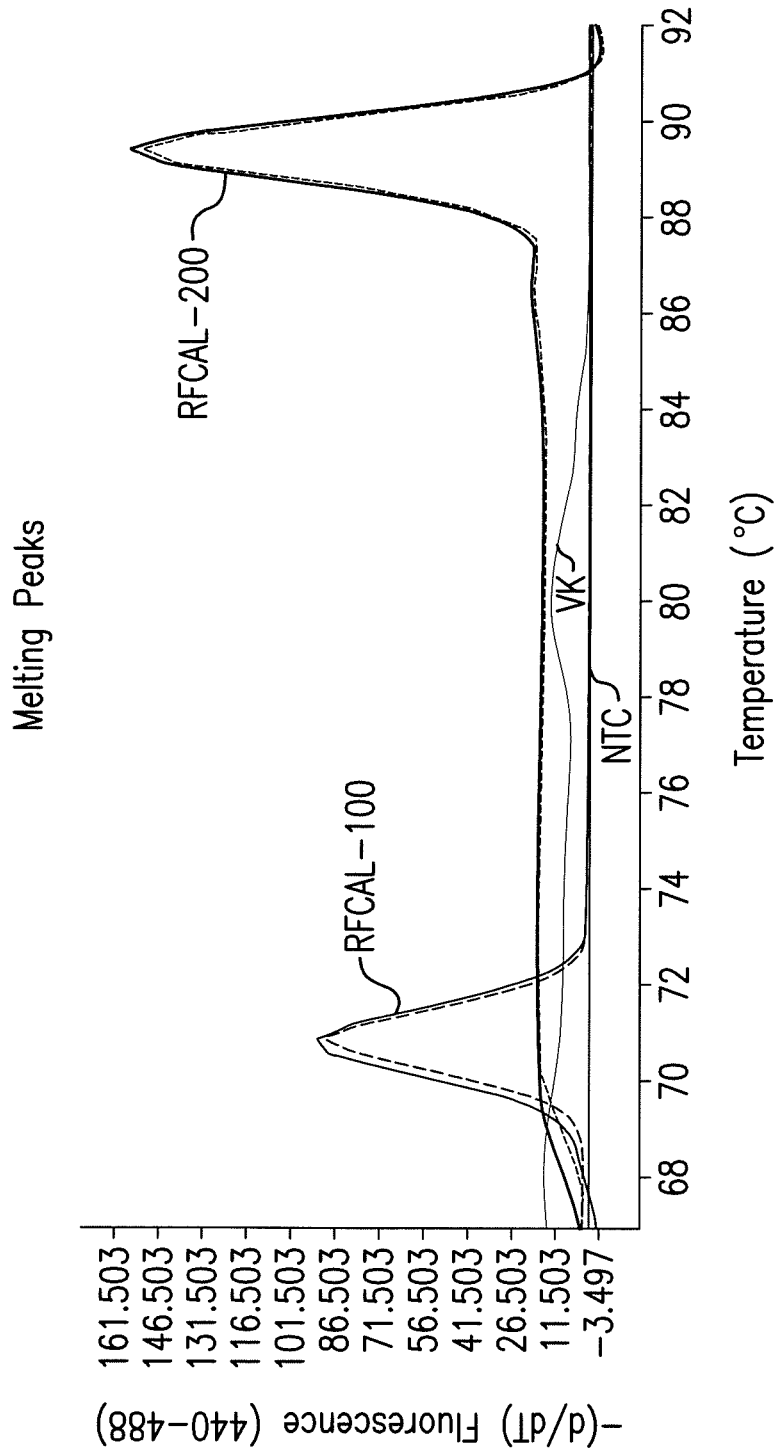
FIG. 14 illustrates a graph depicting the calibrators' product melting on a LC480 cycler platform in accordance with an embodiment of the invention.

Melting peaks for both DNA samples also were successfully obtained. Both presented a single and defined peak that was far apart from each other. RFCAL-100 has a melt temperature $T_M$ around 70° C., and RFCAL-200 has a melt temperature $T_M$ around 90° C. FIG. 14 illustrates thermal melt curves depicting the amplification product of the calibrators melting on a LC480 cycler platform.

Figure 15:
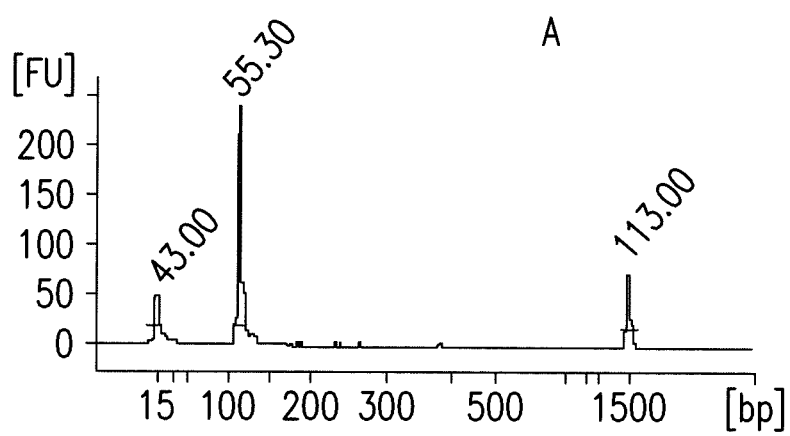
FIG. 15 illustrates a graph depicting the results of RFCAL-100 on a microfluidics-based analysis platform in accordance with an embodiment of the invention.
Figure 16:
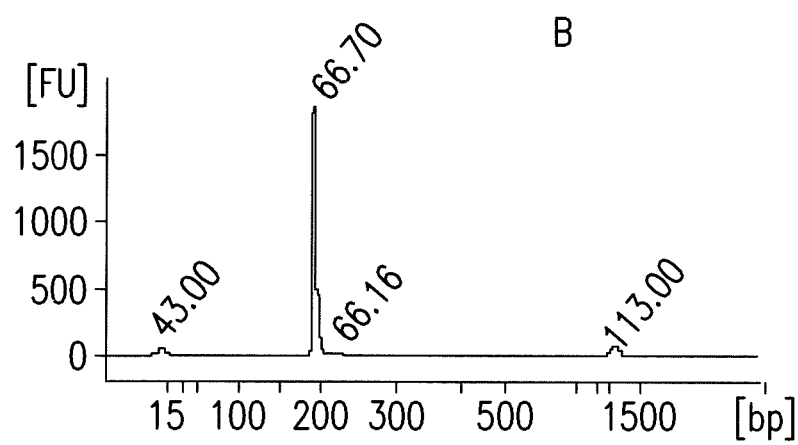
FIG. 16 illustrates a graph depicting the results of RFCAL-200 on a microfluidics-based analysis platform in accordance with an embodiment of the invention.

An aliquot of the PCR product was then checked for target size confirmation using an Agilent Bioanalyzer 2100 microfluidics-based analysis platform. FIG. 15 illustrates the RFCAL-100 analysis results, and FIG. 16 illustrates the RFCAL-200 results.

Expected and observed band size for RFCAL 100 and RFCAL-200 PCR product is shown below.

| Seq. product | Bp expected | Bp observed |
|---|---|---|
| RFCAL-100 | 100 bp | 113 bp |
| RFCAL-200 | 200 bp | 204 bp |

Figure 17:
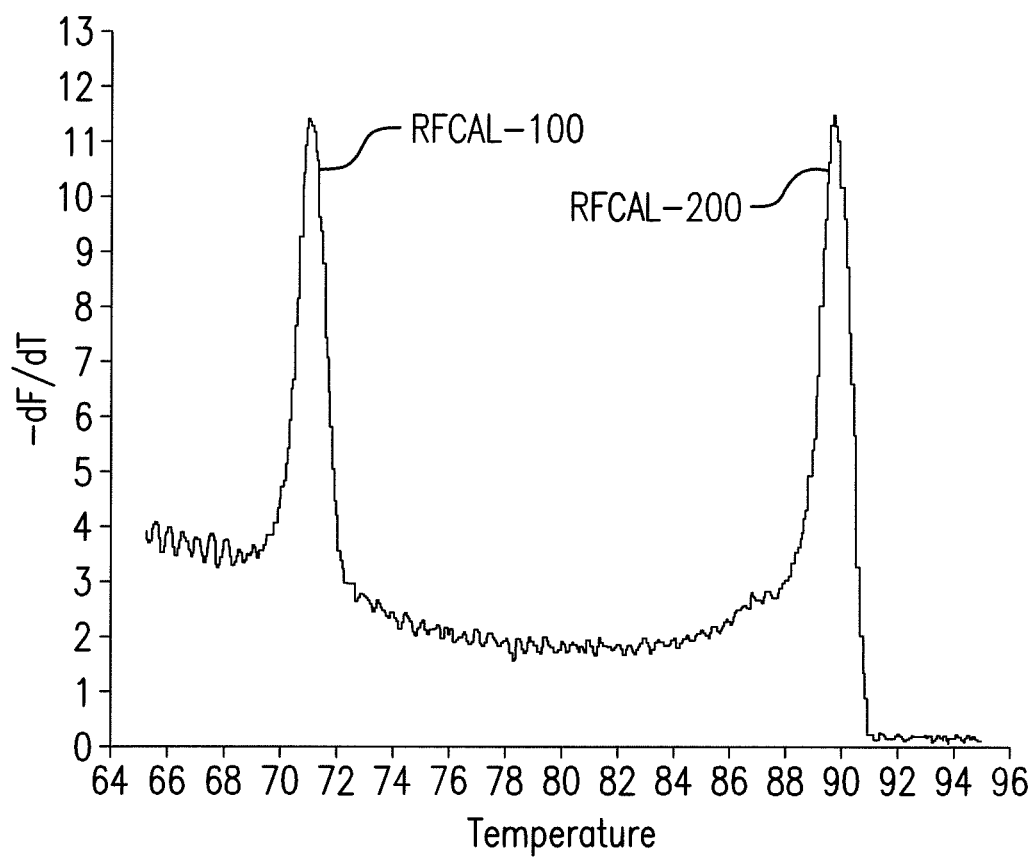
FIG. 17 illustrates a graph depicting the RFCAL-melt profile on Idaho Technologies HR-1 high resolution melter in accordance with an embodiment of the invention.

In a preferred embodiment, RFCAL-100 and RFCAL-200 are added on a 2:1 ratio because RFCAL-100 presents a lower fluorescent values than RFCAL-200. By doing so, RFCAL-100 and RFCAL-200 achieve rough fluorescence equivalence in the final formulation. FIG. 17 illustrates an RFCAL-melt profile for RFCAL-100 and RFCAL-200 on Idaho Technologies HR-1 high-resolution melter with the calibrator formulated in a 2:1 ratio of RF-CAL100 to RFCAL-200. As shown in FIG. 17, the fluorescent values of RFCAL-100 and RFCAL-200 are substantially the same at these ratios. However, it is not necessary that RFCAL-100 and RFCAL-200 achieve rough fluorescence equivalence, and other ratios may be used.

In the exemplary embodiment, the two constructs and respective primers worked as desired. The primers were able to demonstrate a successful amplification of the expected product. Each of their amplification products showed a single peak with high fluorescent values upon melt. Product specificity was confirmed by demonstration of expected fragment sizes on the Bioanalyzer microfluidics-based analysis platform. RFCAL-100 and RFCAL-200 are thus useful for temperature calibration purposes given their performance.

Although the specific examples of UCE and synthetic calibrants have been described above, other calibrants may be used in accordance with aspects of the present invention.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

Non-Limiting Temperature Calibration/Correction Examples

As noted above, the computation from a resistance measurement, R, of a heating sensing element to measured temperature, $T_{mes}$, may take the form of the linear equation:

$$T_{mes} = k_1 R + k_0 \qquad \text{Equation 4}$$

An error in terms $k_1$, or $k_0$ would lead to a bias or shift in the measured temperature relative to the true temperature. Calibrants (i.e., positive control DNA having a known or expected melt temperature) may be used to calculate the temperature compensation to shift the measured temperature closer to the true value.

Single Peak Temperature Calibration with Interpolation

When a single peak amplicon (e.g., derived from the 207 bp UCE sequence) is used as a calibrant (i.e., positive control), a single temperature shift (correction in intercept $k_0$) may be applied to the span of all measured temperatures of a particular melt. In one embodiment, this shift correction value $k'_0$ may be applied to an unknown DNA sample as follows. First, the peak temperatures of a pre UCE melt ($T_m^{pre\ UCE}$) and a post UCE melt ($T_m^{post\ UCE}$) are obtained.

Second, the adjusted temperature of an assay melt that is run in between the two UCEs (i.e., calibrants) is calculated by linear interpolation.

The peak temperatures of the pre UCE amplicon melt ($T_m^{pre\ UCE}$) and the post UCE amplicon melt ($T_m^{post\ UCE}$) may be obtained, for example, in step 304 of the process 300a for calibrating the temperature of a microfluidic channel of a microfluidic device shown in FIG. 3A or in step 316 of the process 300b for calibrating the temperature of a thermal melt shown in FIG. 3B. In other embodiments, the peak temperatures of the pre UCE amplicon melt ($T_m^{pre\ UCE}$) and the post UCE amplicon melt ($T_m^{post\ UCE}$) may be obtained using any suitable approach. For example, one suitable approach is a peak picking approach that obtains $T_m^{pre\ UCE}$ and $T_m^{post\ UCE}$ by (i) using a Savitzky-Golay filter with a predefined window size, polynomial and temperature resolution (e.g., 2° C., $2^{nd}$ order, and 0.01° C. respectively) to obtain the negative derivatives of the pre and post UCE amplicon melts and (ii) finding the temperatures at the maximum negative derivatives of the pre and post UCE amplicon melts. Here, the temperatures at the maximum negative derivatives of the pre and post UCE amplicon melts are $T_m^{pre\ UCE}$ and $T_m^{post\ UCE}$.

In another embodiment, the peak temperatures of the pre UCE amplicon melt ($T_m^{pre\ UCE}$) and the post UCE amplicon melt ($T_m^{post\ UCE}$) may be obtained using a maximal correlation approach. Under the maximal correlation approach, $T_m^{pre\ UCE}$ and $T_m^{post\ UCE}$ are obtained by using the derivative of the melt curve of a calibrant (i.e., positive control) (e.g., shown as a solid line in FIG. 21A) from a calibrated instrument as a reference to which a derivative of a melt curve of the calibrant from one or more subsequent experiments (e.g., shown as a dotted line in FIG. 21A) are shifted. Accordingly, y(x) for the experimental calibrant may be shifted by various dx:

$$y'(x) = y(x-dx) \quad \text{Equation 5}$$

Figure 21A:
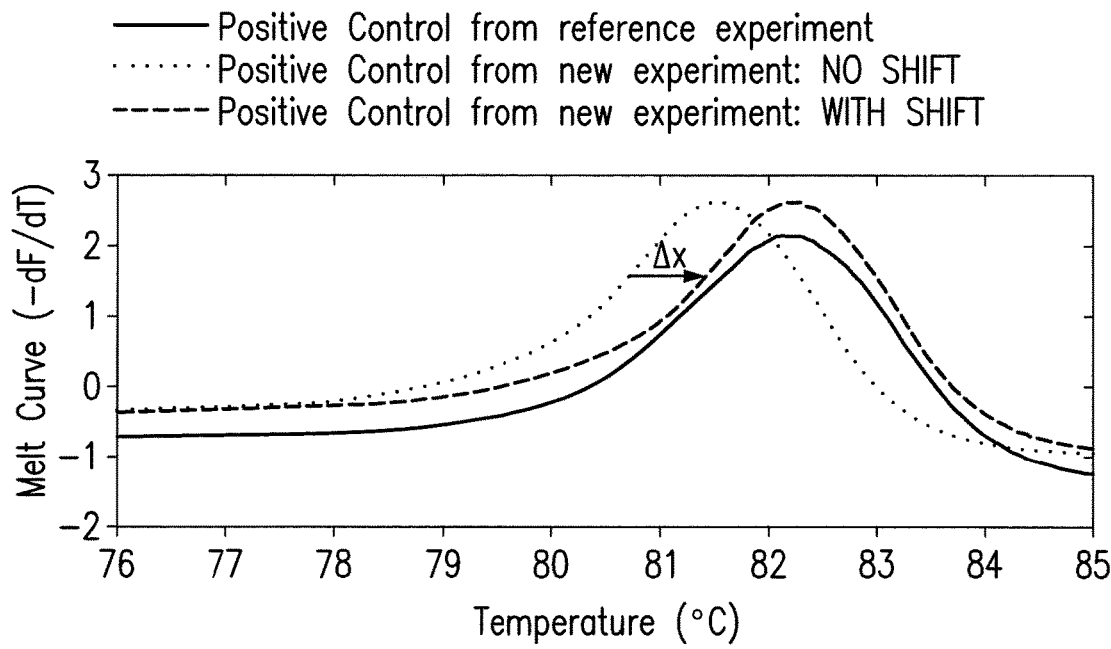
FIG. 21A illustrates calculation of the relative temperature shift of an experimental calibrant relative to reference calibrant from a calibrated instrument in accordance with an embodiment of the invention.
Figure 21B:
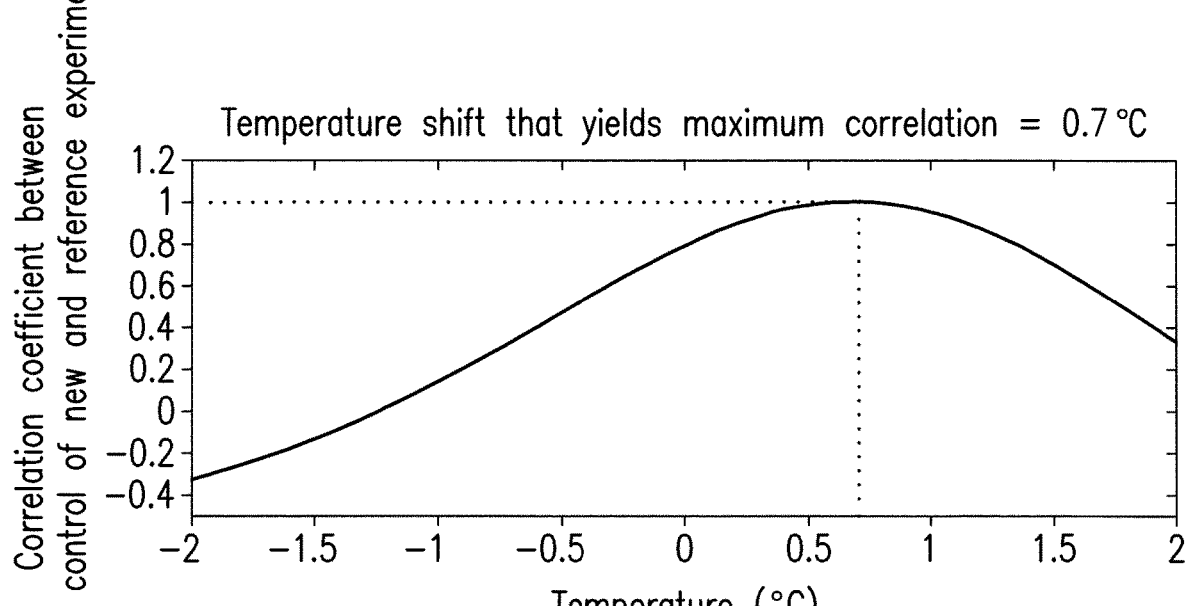
FIG. 21B illustrates calculation of the temperature shift on the experimental calibrant as the shift required to maximize the correlation with the reference calibrant in accordance with an embodiment of the invention.

In this way, the negative derivative of the reference calibrant (e.g., shown as a solid line in FIG. 21A) may be correlated against the shifted calibrant of a subsequent experiment, y'(x), as shown in FIG. 21A. The optimal shift may be given by the dx that maximizes the correlation coefficient as shown in FIG. 21B. In FIG. 21A, the optimal shift results in the dashed line. $T_m^{pre\ UCE}$ and $T_m^{post\ UCE}$ may then be calculated by subtracting the optimal dx from the $T_m$ of the reference UCE. This maximal correlation approach to calculating shifts in $T_m$ may be more robust to noise than the picking the peak alternative, but either method may be used.

Once $T_m^{pre\ UCE}$ and $T_m^{post\ UCE}$ are obtained, the adjusted temperature of an assay melt that is run in between the two UCEs may be calculated by linear interpolation as follows:

$$\Delta T_m^{Assay\ minus\ interpolated\ UCE} = T^{Assay} - T_M^{pre\ UCE} + \frac{(\text{melt\_index}^{Assay} - \text{melt\_index}^{pre\ UCE})}{(\text{melt\_index}^{post\ UCE} - \text{melt\_index}^{pre\ UCE})} (T_m^{post\ UCE} - T_m^{pre\ UCE}) \quad \text{Equation 6}$$

$$T^{Assay,adjusted} = T_m^{reference\ UCE} + \Delta T_m^{Assay\ minus\ interpolated\ UCE} \quad \text{Equation 7}$$

Thus, the calculation for the shift correction value $k'_0$ is:

$$k'_o = T_m^{reference\ UCE} - T_M^{pre\ UCE} + \frac{(\text{melt\_index}^{Assay} - \text{melt\_index}^{pre\ UCE})}{(\text{melt\_index}^{post\ UCE} - \text{melt\_index}^{pre\ UCE})} (T_m^{post\ UCE} - T_m^{pre\ UCE}) \quad \text{Equation 8}$$

and $$T^{Assay,adjusted} = T^{Assay} + k'_o \quad \text{Equation 9}$$

Note that in the equations above, $T_m^{reference\ UCE}$ is the true, known $T_m$ of the UCE taken from the literature or measured from a calibrated instrument, and $T^{Assay}$ is the assay temperature vector or $T_m$ of the assay measured by the experimental instrument. The calculation of the shift correction value using Equation 8 may occur, for example, in step 306 of the process 300a for calibrating the temperature of a microfluidic channel of a microfluidic device shown in FIG. 3A or in step 318 of the process 300b for calibrating the temperature of a thermal melt shown in FIG. 3B. The calculation of the adjusted temperature shown in Equation 9 may occur, for example, in step 308 of the process 300a for calibrating the temperature of a microfluidic channel of a microfluidic device shown in FIG. 3A or in step 320 of the process 300b for calibrating the temperature of a thermal melt shown in FIG. 3B.

Figure 22A:
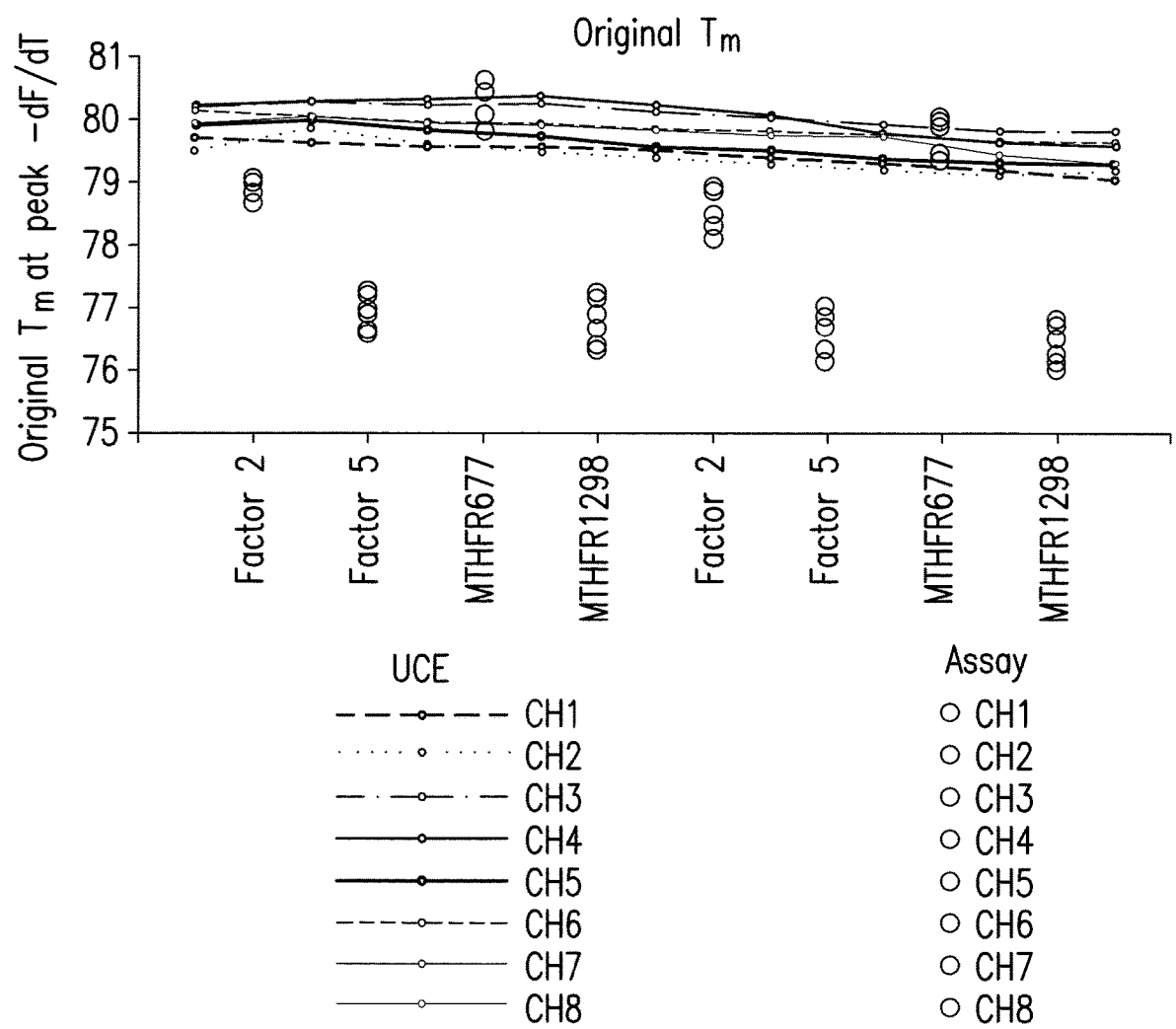
FIG. 22A is a plot illustrating melting temperatures of assays of the same genotype and interlaced UCEs collected from 7 different channels.
Figure 22B:
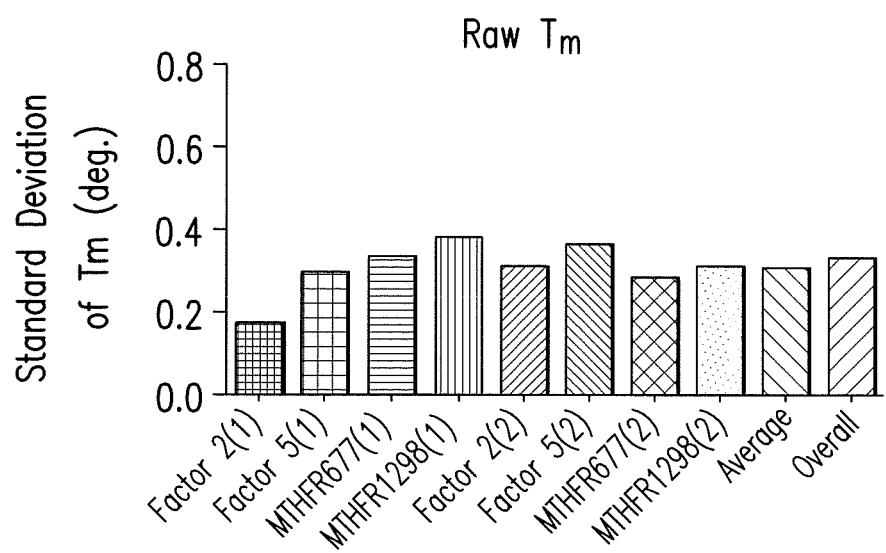
FIG. 22B is a plot illustrating the standard deviation of the assays melted at the same time across the 7 channels in FIG. 22A.
Figure 22C:
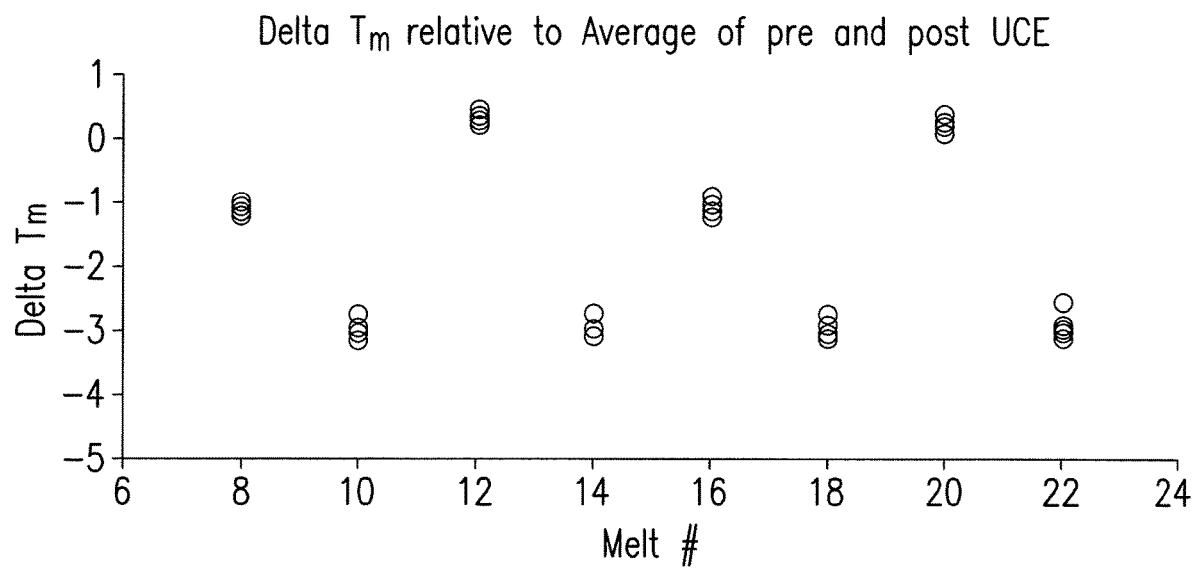
FIG. 22C is a plot illustrating the changes in the melt temperatures of the assays relative to the interpolated UCE melt temperature using the immediately preceding and immediately following UCE.
Figure 22D:
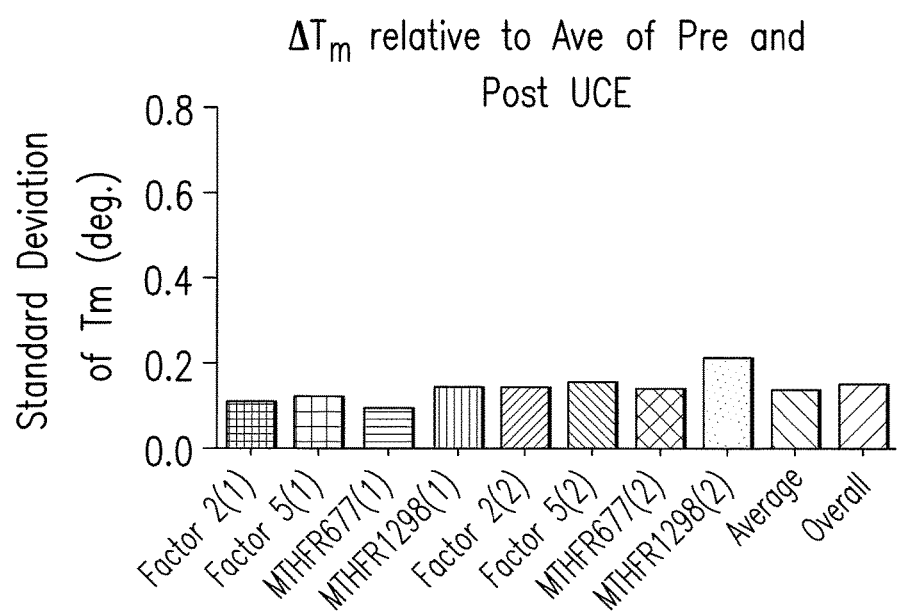
FIG. 22D is a plot illustrating the corresponding standard deviation of the changes in the melt temperatures shown in FIG. 22C.
Figure 22E:
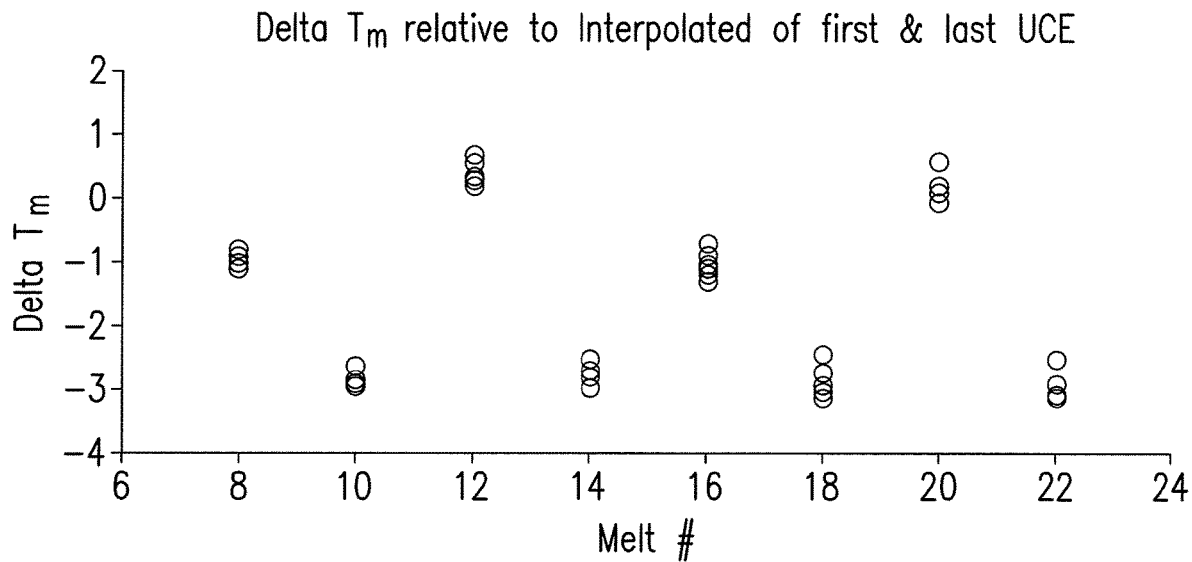
FIG. 22E is a plot illustrating the changes in the melt temperatures of the assays relative to the interpolated UCE Tm using only the first and last UCE.
Figure 22F:
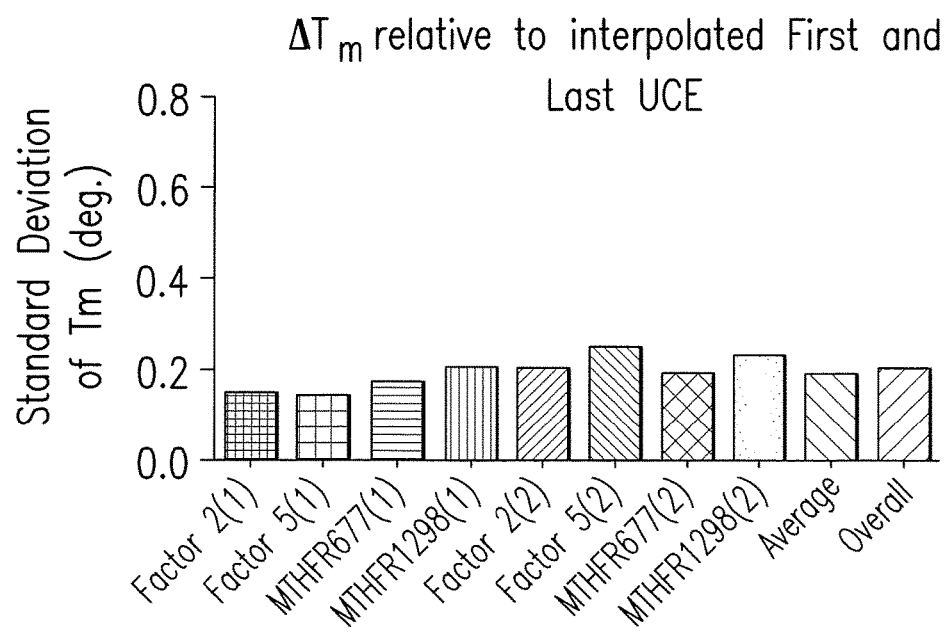
FIG. 22F is a plot illustrating the corresponding standard deviation of changes in the melt temperatures of the assays shown in FIG. 22E.

FIG. 22A is a plot illustrating melting temperatures (Tms) of assays of the same genotype (open circles) and interlaced UCEs (solid points connected by lines) collected from 7 different channels. FIG. 22B is a plot illustrating the standard deviation of the assays melted at the same time across the 7 channels. FIG. 22C is a plot illustrating the changes in the melt temperatures (ΔTms) of the assays relative to the interpolated UCE melt temperature (Tm) using the immediately preceding and immediately following UCE. FIG. 22D is a plot illustrating the corresponding standard deviation of the changes in the melt temperatures (ΔTms) shown in FIG. 22C. FIG. 22E is a plot illustrating the changes in the melt temperatures (ΔTms) of the assays relative to the interpolated UCE Tm using only the first and last UCE. FIG. 22F is a plot illustrating the corresponding standard deviation of changes in the melt temperatures (ΔTms) of the assays shown in FIG. 22E.

As shown in FIGS. 22A-22F, when there is a drift in temperature in a particular channel (as shown by the drifting $T_m$ of the UCEs) or if there is a shift in measured temperature from channel to channel, calculating the adjusted measured temperature of the assay relative to the interpolated Tm of the pre and post UCEs may be used to help reduce the standard deviations of $T_m$s of the assays (of the same genotype) across the channels. In this way, calculating the adjusted measured temperature of the assay relative to the interpolated Tm of the pre and post UCEs may be used to improve the accuracy of a genotype call.

In the example method using a single calibrant/peak set forth above, use of a genomic UCE (e.g., the 207 bp UCE sequence described above) is not necessary. A synthetic sequence (e.g., RFCAL-100 or RFCAL-200) may alternatively be used as the calibrant.

Dual Peak Temperature Calibration

When a dual peak calibrant (e.g., a calibrant comprising RFCAL-100 and RFCAL-200) is used as a positive control, a temperature scaling as well as shift (correction in slope $k_1$ as well as intercept $k_0$) may be applied to the span of all measured temperatures of a particular melt. The description and associated equations of dual peak temperature calibration use the term UCE for convenience. It should be understood that this term refers to any calibrant. For this reason, using a dual peak positive control may lead to more accurate compensation of measured temperature values. In one embodiment, this scale correction $k'_1$, and shift correction value $k'_0$ may be applied to an unknown DNA sample as follows. First, the low and high peak temperatures of an experimental dual peak calibrant (e.g., UCE and/orgenomic and/or synthetic) melt $T_{m\ low}^{UCE}$ and $T_{m\ low}^{UCE}$ are obtained. Second, the adjusted temperature of an assay melt that is run following the experimental positive control is obtained.

The low and high peak temperatures of an experimental dual peak calibrant (e.g., UCE) melt may be obtained, for example, in step 304 of the process 300a for calibrating the temperature of a microfluidic channel of a microfluidic device shown in FIG. 3A or in step 316 of the process 300b for calibrating the temperature of a thermal melt shown in FIG. 3B. The low and high peak temperatures of an experimental dual peak calibrant (e.g., UCE) melt $T_{m\ low}^{UCE}$ and $T_{m\ low}^{UCE}$ may be obtained using any suitable approach. For example, one suitable approach (i) obtains the derivative of the melt curve of the experimental calibrant by using a Savitzky-Golay filter with a predefined window size, polynomial and temperature resolution (e.g., 2° C., $2^{nd}$ order, and 0.01° C. respectively) and (ii) finds the temperatures at the maximum negative derivatives (low and high) of the dual peak calibrant. Here, the temperatures at the maximum negative derivatives (low and high) of the dual peak calibrant are $T_m^{pre\ UCE}$ and $T_m^{post\ UCE}$.

Another suitable approach for obtaining the low and high peak temperatures of an experimental dual peak calibrant melt $T_{m\ low}^{UCE}$ and $T_{m\ high}^{UCE}$ may use the derivative of a melt curve for a dual peak calibrant (i.e., positive control) obtained from a calibrated instrument as a reference. The low temperature and high temperature peaks may be found ($T_{m\ low}^{UCE\ reference}$ and $T_{m\ high}^{UCE\ reference}$) from the reference derivative of the melt curve, and a window (e.g., ±1.5° C.) may be placed around each peak (shown by the dashed line segments of FIG. 23A).

Figure 23A:
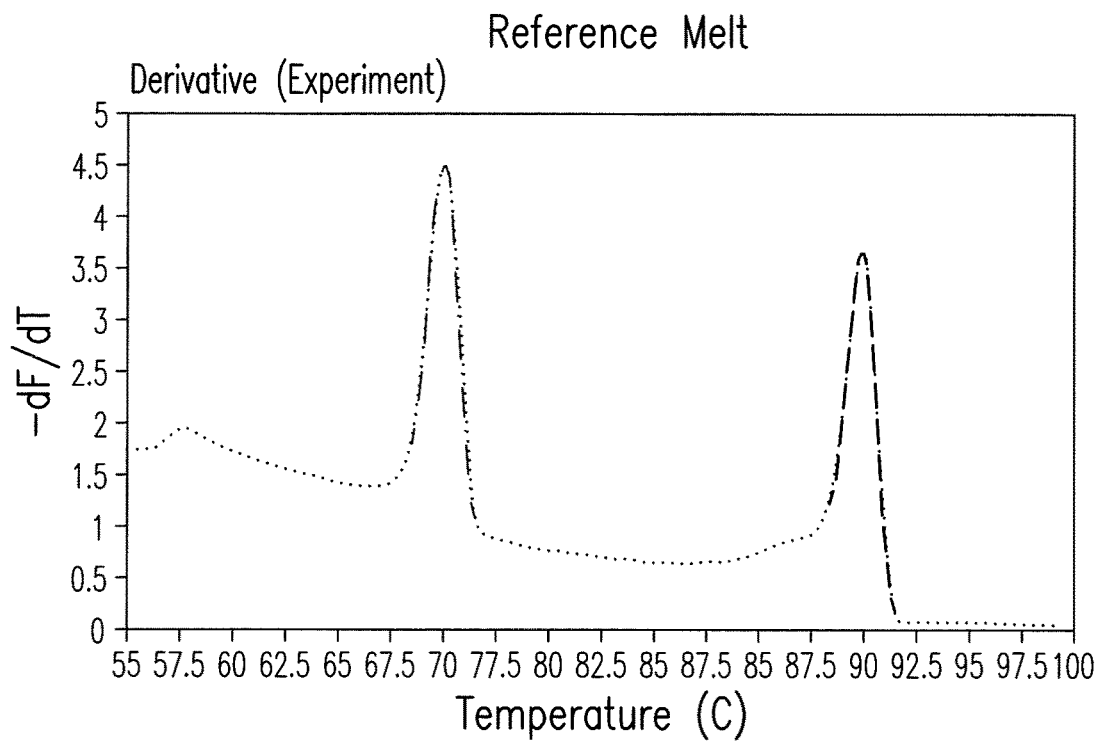
FIG. 23A is a plot illustrating a reference dual peak thermal melt curve from a calibrated instrument.
Figure 23B:
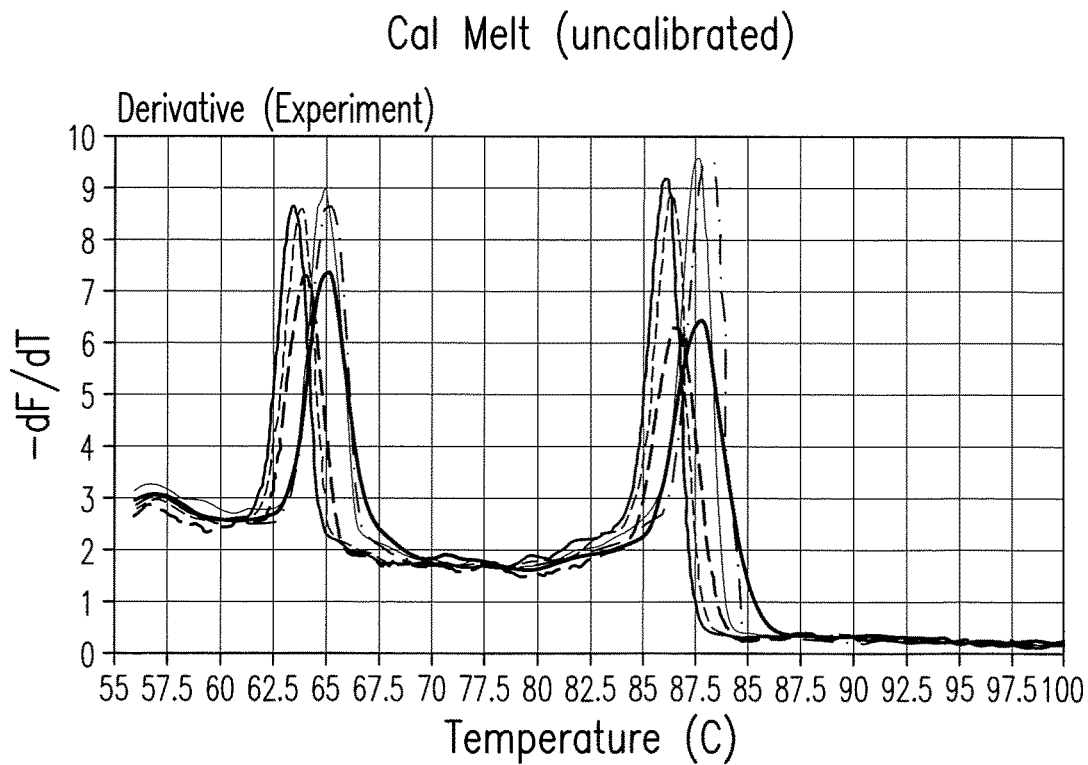
FIG. 23B is a plot illustrating an out of calibration dual peak experimental thermal melt curve.

The negative derivative of the left peak (dashed line portion of FIG. 23A centered around 70° C.) of the reference derivative may be cross-correlated against the negative derivative of the left peak of the experimental calibrant shown in FIG. 23B. The two highest cross-correlation points may be obtained, and the temperature of the first (left) highest cross-correlation point may be taken as $T_{m\ low}^{UCE}$. The negative derivative of the right peak (dashed line portion of FIG. 23A centered around 90° C.) of the reference derivative may be cross-correlated against the negative derivative of the right peak of the experimental calibrant shown in FIG. 23B. The two highest cross-correlation points may be obtained, and the temperature of the second (right) highest cross-correlation point may be taken as $T_{m\ high}^{UCE}$.

Once $T_{m\ low}^{UCE}$ and $T_{m\ high}^{UCE}$ have been obtained, the adjusted temperature of an assay melt that is run before or following the experimental positive control may be obtained by calculating a slope correction factor and an intercept correction factor as follows:

$$\text{slope\_correction\_factor: } k'_1 = \frac{(T_{m\ high}^{UCE\ reference} - T_{m\ low}^{UCE\ reference})}{(T_{m\ high}^{UCE} - T_{m\ low}^{UCE})} \quad \text{Equation 10}$$

$$\text{interecept\_correction\_factor: } k'_0 = T_{m\ high}^{UCE\ reference} - k'_1(T_{m\ high}^{UCE}) \quad \text{Equation 11}$$

The slope correction factor and the intercept correction factor may be calculated, for example, in step 306 of the process 300a for calibrating the temperature of a microfluidic channel of a microfluidic device shown in FIG. 3A or in step 318 of the process 300b for calibrating the temperature of a thermal melt shown in FIG. 3B.

Then, the adjusted temperature may be calculated from the slope correction factor and the intercept correction factor as follows:

$$T^{Assay.adjusted} = k'_1(T^{Assay}) + k'_0 \quad \text{Equation 12}$$

Alternatively, these correction factors may be applied to the resistance values in real time to obtain the recalibrated temperature reading as follows:

$$T^{Assay.adjusted} = k'_1 k_1 R + k'_1 k_0 + k'_0 \quad \text{Equation 13}$$

The calculation of the adjusted temperature shown in either Equation 12 or Equation 13 may occur, for example, in step 308 of the process 300a for calibrating the temperature of a microfluidic channel of a microfluidic device shown in FIG. 3A or in step 320 of the process 300b for calibrating the temperature of a thermal melt shown in FIG. 3B.

Figure 23C:
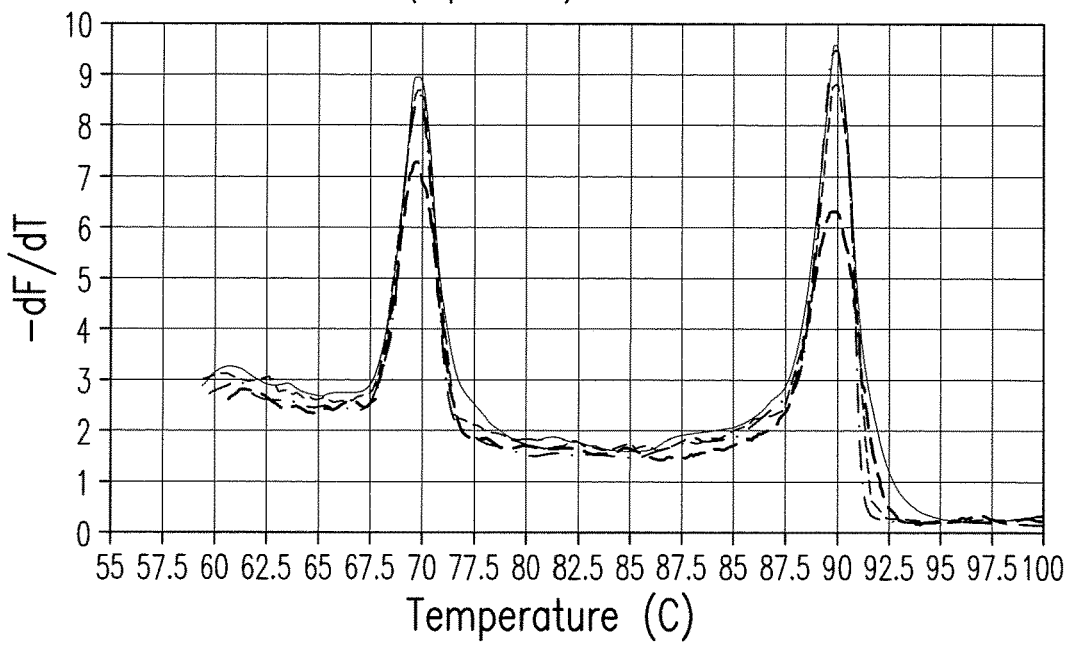
FIG. 23C is a plot illustrating the out of calibration dual peak experimental thermal melt curve shown in FIG. 23B lined up with the reference dual peak thermal melt curve shown in FIG. 23A.
Figure 23D:
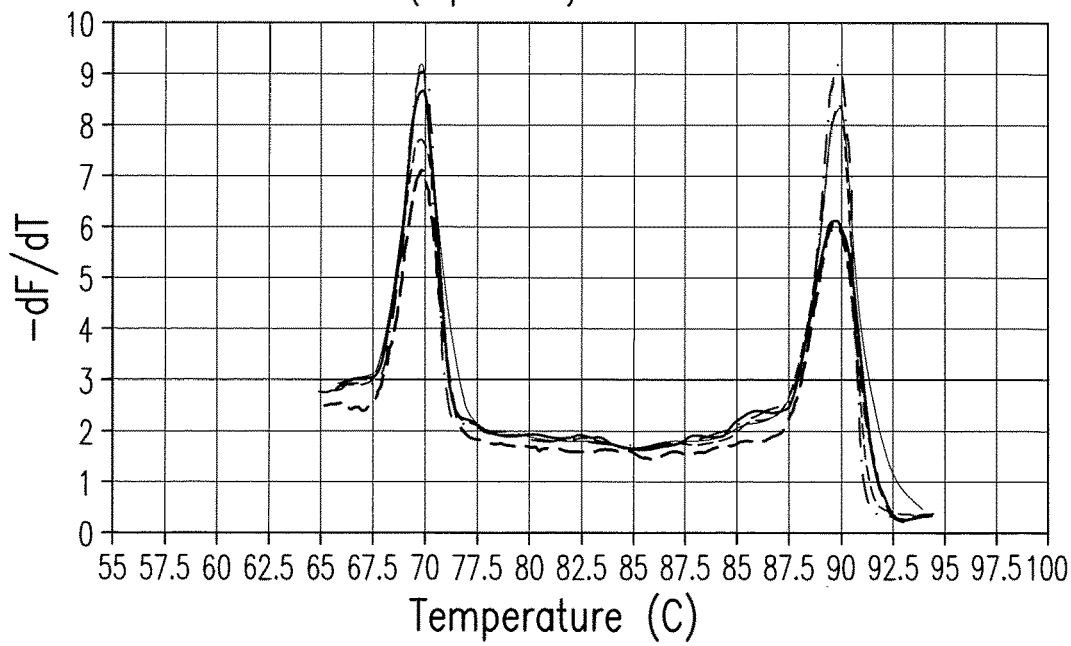
FIG. 23D is a plot illustrating a subsequent melt curve of an independent calibration check melt.
Figure 23E:
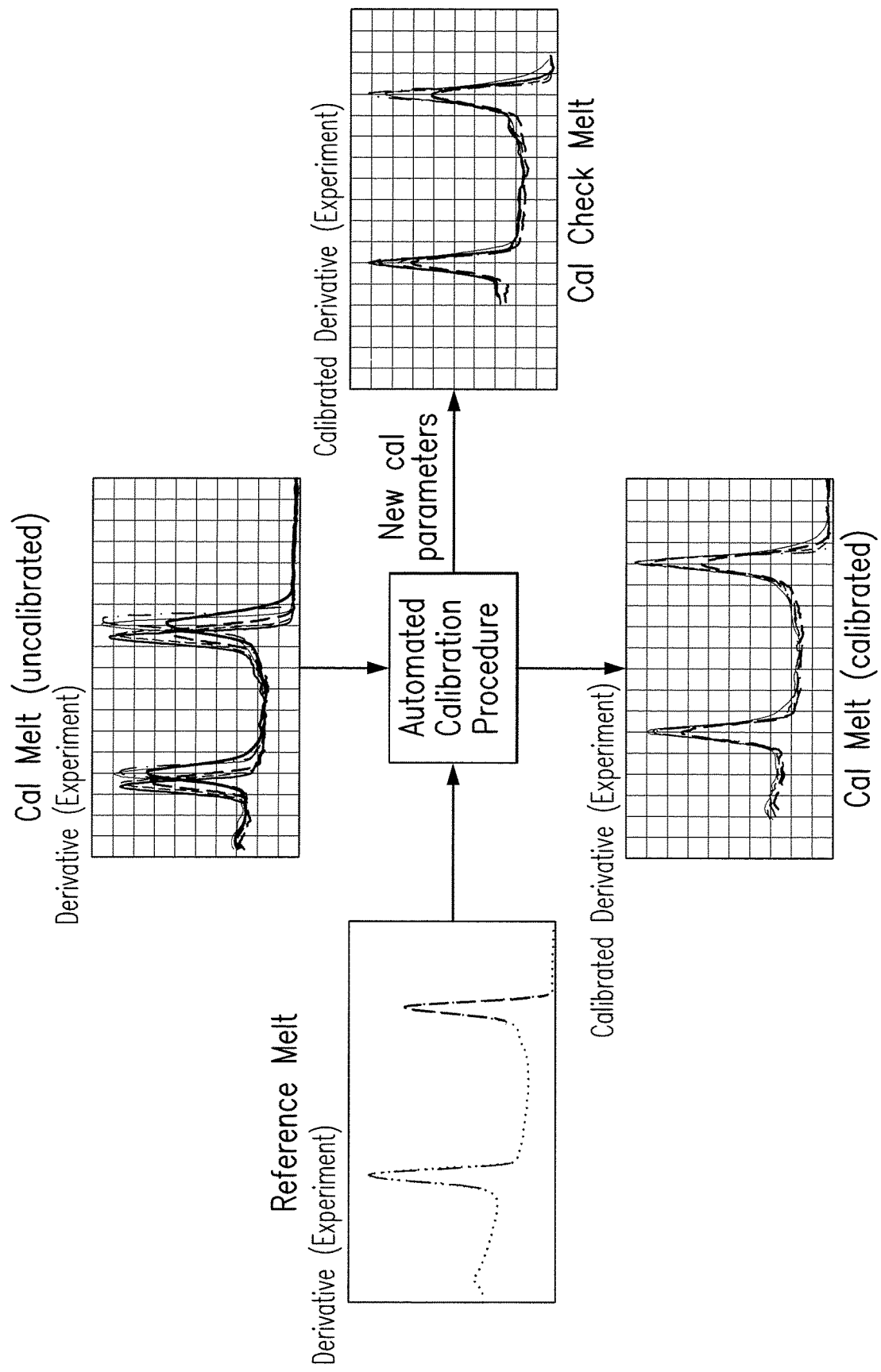
FIG. 23E is a schematic diagram illustrating the functioning of the automatic calibration procedure in accordance with an embodiment of the invention.

As shown in FIG. 23C, using an out of calibration dual peak calibrant (e.g., a calibrant producing the dual peak melt curve shown in FIG. 23B), the recalibration procedure described above may line up the low and high peaks with the low and high peaks from the reference melt of the calibrator (e.g., the reference melt shown in FIG. 23A). As illustrated in FIG. 23D, the subsequent melt of an independent calibration check melt shows that this recalibration procedure works on subsequent melts. FIG. 23E is a schematic diagram illustrating the functioning of the automatic calibration procedure using a dual peak calibrant.

As shown in the temperature calibration examples set forth above, calibrants (i.e., positive control DNA) having known or expected melt temperatures and producing single or dual peak melt curves may be used to intermittently account for calibration drift in the instrument.

What is claimed is:

1. A method of calibrating a temperature sensor measuring the temperature of a thermal melt in a microfluidic channel present in a microfluidic system, the method comprising:
   (a) introducing into the microfluidic channel a sample consisting essentially of human genomic DNA, and reagents necessary for amplifying the human genomic DNA, comprising a polymerase, dNTPs, a fluorescent dye, at least a pair of primers for one or more nucleic acid sequences of interest found within the human genomic DNA and a pair of primers for a calibrant amplified from the human genomic DNA, wherein the primers for the calibrant are (i) SEQ ID Nos: 7 and 8 or (ii) SEQ ID Nos: 9 and 10;
   (b) amplifying a portion of the human genomic DNA in the sample to produce a calibrant amplicon and an amplicon of the one or more nucleic acid sequences of interest;
   (c) melting the amplicons, where in a detector under control of a controller detects fluorescence emissions of each of the amplicons, and the controller uses the fluorescence emissions and corresponding readings of the temperature sensor to determine a melting temperature of each of the amplicons;
   (d) causing the controller to compare the determined melting temperature of the calibrant amplicon with an expected melting temperature of the calibrant amplicon; and
   (e) where the determined melting temperature of the calibrant amplicon differs from the expected melting temperature of the calibrant amplicon, causing the controller to determine one or more correction factors and to determine a corrected melting temperature of the amplicon of the one or more nucleic acid sequences of interest.

2. The method of claim 1, wherein a derivative of a melt curve of the melting of the calibrant amplicon exhibits a single peak.

3. The method of claim 1, further comprising providing a control to validate that amplification has occurred, wherein a melt curve depicting the detected fluorescence emissions from the calibrant amplicon serves as a control to validate amplification occurred.

4. The method of claim 1, wherein the pair of primers for the calibrant do not affect amplification of the one or more nucleic acid sequences of interest.

5. The method of claim 1, wherein the determining the melting temperature of each of the amplicons comprises:
   obtaining a derivative of a melt curve of the melting of each of the amplicon by the controller applying a Savitzky-Golay filter to the fluorescence data obrained during the melting; and
   finding the temperatures at the maximum negative derivatives of the derivative of the melt curve.

6. The method of claim 5, wherein the determining the melting temperature of the amplicon calibrant comprises:
   cross-correlating peaks of a derivative of a reference melt curve against peaks of a derivative of a melt curve of the melting of the amplicon calibrant; and
   selecting the temperatures having the highest correlation as the melting temperature of the amplicon calibrant.

7. The method of claim 5, wherein the comparing the determined melting temperature of the amplicon calibrant with the respective expected melting temperature of the amplicon calibrant comprises the controller calculating a slope correction factor and an intercept correction factor using the expected melting temperature of the amplicon calibrant according to:

$$\text{slope\_correction\_factor: } k'_1 = \frac{\left(T_{m\,high}^{UCE\,reference} - T_{m\,low}^{UCE\,reference}\right)}{\left(T_{m\,high}^{UCE} - T_{m\,low}^{UCE}\right)};$$

$$\text{intercept\_correction\_factor: } k'_0 = T_{m\,high}^{UCE\,reference} - k'_1(T_{m\,high}^{UCE}),$$

where $T_{m\,low}^{UCE}$ and $T_{m\,high}^{UCE}$ are the low and high peak temperatures measured by the temperature sensor during the melt, and $T_{m\,low}^{UCE\,reference}$ and $T_{m\,high}^{UCE\,reference}$ are expected melting temperatures of the calibrant amplicons.

8. The method of claim 1, wherein the introducing into the microfluidic channel reagents comprising at least a pair of primers for one or more nucleic acid sequences of interest found in human genomic DNA and a pair of primers for a calibrant occurs with the at least a pair of primers for one or more human nucleic acid sequences of interest and the pair of primers for a calibrant being introduced into the microfluidic channel in separate fluid segments.

9. A method of calibrating a temperature sensor measuring the temperature of a microfluidic channel present in a microfluidic system, the method comprising:
(a) melting one or more calibrant amplicons, wherein the one or more calibrant amplicons are human genomic DNA amplicons amplified by the primers (i) SEQ ID Nos: 7 and 8 or (ii) SEQ ID Nos: 9 and 10 in an amplification reaction comprising a fluorescent dye, wherein a detector under control of a controller detects fluorescence emissions of the one or more calibrant amplicons and the controller uses the fluorescence emissions and corresponding readings of a temperatures sensor to determine a melting temperature of each of the calibrant amplicons;
(b) causing the controller to compare the determined melting temperature of each of the one or more calibrant amplicons with a respective expected melting temperature of each of the one or more calibrant amplicons; and
(c) causing the controller to determine one or more correction factors and causing the controller to calibrate the temperature of the microfluidic channel detected by the temperature sensor.

10. The method of claim 9, wherein the melting and determining comprises melting two or more calibrant amplicons and a controller determining a melting temperature of each of the calibrant amplicons;
the comparing comprises having a controller compare the determined melting temperature of each of the two or more calibrant amplicons with a respective expected melting temperature of each of the two or more calibrant amplicons; and
the calibrating comprises the controller calibrating the microfluidic channel based on the comparison of the determined melting temperature of each of the two or calibrant amplicons with the respective expected melting temperature of each of the two or more calibrant amplicons.

11. The method of claim 10, wherein the determining the melting temperature of each of the two more calibrant amplicons comprises:
obtaining a derivative of a melt curve of the melting of the two or more calibrant amplicons by the controller applying a Savitzky-Golay filter to the fluorescence data obrained during the melting; and
finding the temperatures at the maximum negative derivatives of the derivative of the melt curve.

12. The method of claim 11, wherein the determining the melting temperature of each of the two more calibrant amplicons comprises:
cross-correlating peaks of a derivative of a reference melt curve against peaks of a derivative of a melt curve of the melting of the two or more calibrant amplicons; and
selecting the temperatures having the highest correlation as the melting temperatures of the two more calibrant amplicons.

13. The method of claim 11, wherein the comparing the determined melting temperature of each of the two or more calibrant amplicons with the respective expected melting temperature of each of the two or more calibrant amplicons comprises calculating a slope correction factor and an intercept correction factor.

14. The method of claim 13, wherein the calibrating comprises the controller calculating an adjusted temperature using the calculated slope correction factor and the calculated intercept correction factor according to:

$$T^{Assay, adjusted} = k'_1(T^{Assay}) + k'_0;$$

$$\text{slope\_correction\_factor: } k'_1 = \frac{\left(T_{m\,high}^{UCE\,reference} - T_{m\,low}^{UCE\,reference}\right)}{\left(T_{m\,high}^{UCE} - T_{m\,low}^{UCE}\right)};$$

$$\text{intercept\_correction\_factor: } k'_0 = T_{m\,high}^{UCE\,reference} - k'_1(T_{m\,high}^{UCE}),$$

where $T_{m\,low}^{UCE}$ and $T_{m\,high}^{UCE}$ are the low and high peak temperatures measured by the temperature sensor during the melt, and $T_{m\,low}^{UCE\,reference}$ and $T_{m\,high}^{UCE\,reference}$ are expected melting temperatures of the calibrant amplicons.

15. The method of claim 10, wherein a derivative of a melt curve of the melting of the one or more calibrant amplicons exhibits a single peak.

16. The method of claim 15, wherein the melting the one or more calibrant amplicons comprises a first melting of the one or more calibrant amplicons and a second melting of the one or more calibrant amplicons, and
the determining the melting temperature of each of the one or more calibrant amplicons comprises (i) determining a first temperature corresponding to a peak of the derivative of the melt curve of the first melting of the one or more calibrant amplicons and (ii) determining a second temperature corresponding to a peak of the derivative of the melt curve of the second melting of the one or more calibrant amplicons.

17. The method of claim 16, wherein the calibrating comprises the controller calculating a temperature adjustment by a linear interpolation of the first and second temperatures.

* * * * *

SEQUENCE LISTING

<160> NUMBER OF SEQ ID NOS: 12

<210> SEQ ID NO 1
<211> LENGTH: 207
<212> TYPE: DNA
<213> ORGANISM: Homo sapiens

<400> SEQUENCE: 1
tgatcccgga ctctatgaat tattgatgag atatgagcgt tgatttcccc tttcaggatg    60

```
caaactccat tatattgtta aaatggcgat ttaatcgttg agaatagctt tggtgtgggt      120 ttttcccc aactcatttg cgcctccttc cttttcattt aactctctta attaaatcct      180
ttaacagatt ttaatcactt tttggag                                         207

<210> SEQ ID NO 2
<211> LENGTH: 20
<212> TYPE: DNA
<213> ORGANISM: Homo sapiens

<400> SEQUENCE: 2
cctttcagga tgcaaactcc                                                  20

<210> SEQ ID NO 3
<211> LENGTH: 21
<212> TYPE: DNA
<213> ORGANISM: Homo sapiens

<400> SEQUENCE: 3
cccacaccaa agctattctc a                                                21

<210> SEQ ID NO 4
<211> LENGTH: 71
<212> TYPE: DNA
<213> ORGANISM: Homo sapiens

<400> SEQUENCE: 4
cctttcagga tgcaaactcc attatattgt taaaatggcg atttaatcgt tgagaatagc      60
tttggtgtgg g                                                           71

<210> SEQ ID NO 5
<211> LENGTH: 100
<212> TYPE: DNA
<213> ORGANISM: Artificial Sequence
<220> FEATURE:
<223> OTHER INFORMATION: oligonucleotide thermal melt calibrant

<400> SEQUENCE: 5
tattaattct aataatgaaa cattatttaa aaaataagta tgataaagta taatttaatg      60
aattatctat taattgaact aaatgagaga ttccaatatt                           100

<210> SEQ ID NO 6
<211> LENGTH: 200
<212> TYPE: DNA
<213> ORGANISM: Artificial Sequence
<220> FEATURE:
<223> OTHER INFORMATION: oligonucleotide thermal melt calibrant

<400> SEQUENCE: 6
cgttcgggaa tgattccggt agcgctaaag gtccatagca cgtgcatcgc aacctggcgt      60
gcgttcagct tgacgaccgc ttggcgctaa ggtgctggcc gcgtgctaag ttgaagcggc     120
tgcactgctg caaggacgat tacgagcgg gcggcctggg gggagcacta ccccatcgac     180
ccgtacagga acactctata                                                 200

<210> SEQ ID NO 7
<211> LENGTH: 20
<212> TYPE: DNA
<213> ORGANISM: Artificial Sequence
<220> FEATURE:
<223> OTHER INFORMATION: oligonculeotide primer

<400> SEQUENCE: 7
```
tattaattct aataatgaaa                                           20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
aatattggaa tctctcattt                                           20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
cgttcgggaa tgattccggt                                           20

<210> SEQ ID NO 10
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 10
tatagagtgt tcctgtacgg gt                                        22

<210> SEQ ID NO 11
<211> LENGTH: 3192
<212> TYPE: DNA
<213> ORGANISM: Artificial Sequence
<220> FEATURE:
<223> OTHER INFORMATION: RFCAL-100 vector

<400> SEQUENCE: 11
gcgcccaata cgcaaaccgc ctctccccgc gcgttggccg attcattaat gcagctggca     60
cgacaggttt cccgactgga aagcgggcag tgagcgcaac gcaattaatg tgagttagct    120
cactcattag gcaccccagg ctttacactt tatgcttccg gctcgtatgt tgtgtggaat    180
tgtgagcggc agcccctca gcaatattgg aatctctcat ttagttcaat taatagataa    240
ttcattaaat tatactttat catacttatt ttttaaataa tgtttcatta ttagaattaa    300
tagctgaggg gctggcaagt gtagcggtca cgctgcgcgt aaccaccaca cccgccgcgc    360
ttaatgcgcc gctacagggc gcgtcaggtg gcacttttcg gggaaatgtg cgcggaaccc    420
ctatttgttt attttcctaa atacattcaa atatgtatcc gctcatgaga caataaccct    480
gataaatgct tcaataatat tgaaaaagga agagtatgag tattcaacat ttccgtgtcg    540
cccttattcc cttttttgcg gcattttgcc ttcctgtttt tgctcaccca gaaacgctgg    600
tgaaagtaaa agatgctgaa gatcagttgg gtgcacgagt gggttacatc gaactggatc    660
tcaacagcgg taagatcctt gagagttttc gccccgaaga acgttttcca atgatgagca    720
cttttaaagt tctgctatgt ggcgcggtat tatcccgtat tgacgccggg caagagcaac    780
tcggtcgccg catacactat tctcagaatg acttggttga gtactcacca gtcacagaaa    840
agcatcttac ggatggcatg acagtaagag aattatgcag tgctgccata accatgagtg    900

```
ataacactgc ggccaactta cttctgacaa cgatcggagg accgaaggag ctaaccgctt    960
ttttgcacaa catgggggat catgtaactc gccttgatcg ttgggaaccg gagctgaatg   1020
aagccatacc aaacgacgag cgtgacacca cgatgcctgt agcaatggca acaacgttgc   1080
gcaaactatt aactggcgaa ctacttactc tagcttcccg gcaacaatta atagactgga   1140
tggaggcgga taaagttgca ggaccacttc tgcgctcggc ccttccggct ggctggttta   1200
ttgctgataa atctggagcc ggtgagcgtg gtctcgcgg tatcattgca gcactggggc    1260
cagatggtaa gccctcccgt atcgtagtta tctacacgac ggggagtcag gcaactatgg   1320
atgaacgaaa tagacagatc gctgagatag gtgcctcact gattaagcat tggtaactgt   1380
cagaccaagt ttactcatat atactttaga ttgatttaaa acttcatttt taatttaaaa   1440
ggatctaggt gaagatcctt tttgataatc tcatgaacaa taaaactgtc tgcttacata   1500
aacagtaata caagggggtgt tatgagccat attcaacggg aaacgtcttg ctctaggccg   1560
cgattaaatt ccaacatgga tgctgattta tatgggtata atgggctcg cgataatgtc    1620
gggcaatcag gtgcgacaat ctatcgattg tatgggaagc ccgatgcgcc agagttgttt   1680
ctgaaacatg gcaaaggtag cgttgccaat gatgttacag atgagatggt cagactaaac   1740
tggctgacgg aatttatgcc tcttccgacc atcaagcatt ttatccgtac tcctgatgat   1800
gcatggttac tcaccactgc gatccccggg aaaacagcat tccaggtatt agaagaatat   1860
cctgattcag gtgaaaatat tgttgatgcg ctggcagtgt tcctgcgccg gttgcattcg   1920
attcctgttt gtaattgtcc ttttaacagc gatcgcgtat tcgtctcgc tcaggcgcaa    1980
tcacgaatga ataacggttt ggttgatgcg agtgattttg atgacgagcg taatggctgg   2040
cctgttgaac aagtctggaa agaaatgcat aaacttttgc cattctcacc ggattcagtc   2100
gtcactcatg gtgatttctc acttgataac cttattttg acgaggggaa attaataggt    2160
tgtattgatg ttggacgagt cggaatcgca gaccgatacc aggatcttgc catcctatgg   2220
aactgcctcg gtgagttttc tccttcatta cagaaacggc ttttttcaaaa atatggtatt  2280
gataatcctg atatgaataa attgcagttt catttgatgc tcgatgagtt tttctaagaa   2340
ttaattcatg accaaaatcc cttaacgtga gttttcgttc cactgagcgt cagacccgt    2400
agaaaagatc aaaggatctt cttgagatcc ttttttttctg cgcgtaatct gctgcttgca   2460
aacaaaaaaa ccaccgctac cagcggtggt ttgtttgccg gatcaagagc taccaactct   2520
ttttccgaag gtaactggct tcagcagagc gcagatacca atactgtcc ttctagtgta    2580
gccgtagtta ggccaccact tcaagaactc tgtagcaccg cctacatacc tcgctctgct   2640
aatcctgtta ccagtggctg ctgccagtgg cgataagtcg tgtcttaccg ggttggactc   2700
aagacgatag ttaccggata aggcgcagcg gtcgggctga acggggggtt cgtgcacaca   2760
gcccagcttg gagcgaacga cctacaccga actgagatac ctacagcgtg agctatgaga   2820
aagcgccacg cttcccgaag ggagaaaggc ggacaggtat ccggtaagcg cagggtcgg    2880
aacaggagag cgcacgaggg agcttccagg gggaaacgcc tggtatcttt atagtcctgt   2940
cgggtttcgc cacctctgac ttgagcgtcg atttttgtga tgctcgtcag gggggcggag   3000
cctatggaaa aacgccagca acgcggcctt tttacggttc ctggccttt gctggccttt    3060
tgctcacatg ttctttcctg cgttatcccc tgattctgtg ataaccgta ttaccgcctt    3120
tgagtgagct gataccgctc gccgcagccg aacgaccgag cgcagcgagt cagtgagcga   3180
ggaagcggaa ga                                                        3192
```

<210> SEQ ID NO 12
<211> LENGTH: 3292
<212> TYPE: DNA
<213> ORGANISM: Artificial Sequence
<220> FEATURE:
<223> OTHER INFORMATION: RFCAL-200 vector

<400> SEQUENCE: 12

| | | | | | |
|---|---|---|---|---|---|
| gcgcccaata | cgcaaaccgc | ctctccccgc | gcgttggccg | attcattaat | gcagctggca | 60 |
| cgacaggttt | cccgactgga | aagcgggcag | tgagcgcaac | gcaattaatg | tgagttagct | 120 |
| cactcattag | gcaccccagg | ctttacactt | tatgcttccg | gctcgtatgt | tgtgtggaat | 180 |
| tgtgagcggc | cagcccctca | gctatagagt | gttcctgtac | gggtcgatgg | ggtagtgctc | 240 |
| cccccaggcc | gcccgctccg | taatcgtcct | tgcagcagtg | cagccgcttc | aacttagcac | 300 |
| gcggccagca | ccttagcgcc | aagcggtcgt | caagctgaac | gcacgccagg | ttgcgatgca | 360 |
| cgtgctatgg | acctttagcg | ctaccggaat | cattcccgaa | cggctgaggg | gctggcaagt | 420 |
| gtagcggtca | cgctgcgcgt | aaccaccaca | cccgccgcgc | ttaatgcgcc | gctacagggc | 480 |
| gcgtcaggtg | gcacttttcg | gggaaatgtg | cgcggaaccc | ctatttgttt | attttttctaa | 540 |
| atacattcaa | atatgtatcc | gctcatgaga | caataaccct | gataaatgct | tcaataatat | 600 |
| tgaaaaagga | agagtatgag | tattcaacat | ttccgtgtcg | cccttattcc | cttttttgcg | 660 |
| gcatttgcc | ttcctgtttt | tgctcaccca | gaaacgctgg | tgaaagtaaa | agatgctgaa | 720 |
| gatcagttgg | gtgcacgagt | gggttacatc | gaactggatc | tcaacagcgg | taagatcctt | 780 |
| gagagttttc | gccccgaaga | acgttttcca | atgatgagca | cttttaaagt | tctgctatgt | 840 |
| ggcgcggtat | tatcccgtat | tgacgccggg | caagagcaac | tcggtcgccg | catacactat | 900 |
| tctcagaatg | acttggttga | gtactcacca | gtcacagaaa | agcatcttac | ggatggcatg | 960 |
| acagtaagag | aattatgcag | tgctgccata | accatgagtg | ataacactgc | ggccaactta | 1020 |
| cttctgacaa | cgatcggagg | accgaaggag | ctaaccgctt | ttttgcacaa | catgggggat | 1080 |
| catgtaactc | gccttgatcg | ttgggaaccg | gagctgaatg | aagccatacc | aaacgacgag | 1140 |
| cgtgacacca | cgatgcctgt | agcaatggca | acaacgttgc | gcaaactatt | aactggcgaa | 1200 |
| ctacttactc | tagcttcccg | gcaacaatta | atagactgga | tggaggcgga | taaagttgca | 1260 |
| ggaccacttc | tgcgctcggc | ccttccggct | ggctggttta | ttgctgataa | atctggagcc | 1320 |
| ggtgagcgtg | ggtctcgcgg | tatcattgca | gcactgggc | cagatggtaa | gccctcccgt | 1380 |
| atcgtagtta | tctacacgac | ggggagtcag | gcaactatgg | atgaacgaaa | tagacagatc | 1440 |
| gctgagatag | gtgcctcact | gattaagcat | tggtaactgt | cagaccaagt | ttactcatat | 1500 |
| atactttaga | ttgatttaaa | acttcatttt | taatttaaaa | ggatctaggt | gaagatcctt | 1560 |
| tttgataatc | tcatgaacaa | taaaactgtc | tgcttacata | aacagtaata | caaggggtgt | 1620 |
| tatgagccat | attcaacggg | aaacgtcttg | ctctaggccg | cgattaaatt | ccaacatgga | 1680 |
| tgctgattta | tatgggtata | aatgggctcg | cgataatgtc | gggcaatcag | gtgcgacaat | 1740 |
| ctatcgattg | tatgggaagc | ccgatgcgcc | agagttgttt | ctgaaacatg | gcaaaggtag | 1800 |
| cgttgccaat | gatgttacag | atgagatggt | cagactaaac | tggctgacgg | aatttatgcc | 1860 |
| tcttccgacc | atcaagcatt | ttatccgtac | tcctgatgat | gcatggttac | tcaccactgc | 1920 |
| gatccccggg | aaaacagcat | tccaggtatt | agaagaatat | cctgattcag | gtgaaaatat | 1980 |
| tgttgatgcg | ctggcagtgt | tcctgcgccg | gttgcattcg | attcctgttt | gtaattgtcc | 2040 |
| ttttaacagc | gatcgcgtat | ttcgtctcgc | tcaggcgcaa | tcacgaatga | ataacggttt | 2100 |

```
                                                  -continued
ggttgatgcg agtgatttg atgacgagcg taatggctgg cctgttgaac aagtctggaa    2160
agaaatgcat aaacttttgc cattctcacc ggattcagtc gtcactcatg gtgatttctc    2220
acttgataac cttattttg acgagggaa attaataggt tgtattgatg ttggacgagt     2280
cggaatcgca gaccgatacc aggatcttgc catcctatgg aactgcctcg gtgagttttc   2340
tccttcatta cagaaacggc tttttcaaaa atatggtatt gataatcctg atatgaataa   2400
attgcagttt catttgatgc tcgatgagtt tttctaagaa ttaattcatg accaaaatcc   2460
cttaacgtga gttttcgttc cactgagcgt cagacccgt agaaaagatc aaaggatctt    2520
cttgagatcc ttttttctg cgcgtaatct gctgcttgca aacaaaaaaa ccaccgctac    2580
cagcggtggt ttgtttgccg gatcaagagc taccaactct ttttccgaag gtaactggct   2640
tcagcagagc gcagatacca aatactgtcc ttctagtgta gccgtagtta ggccaccact   2700
tcaagaactc tgtagcaccg cctacatacc tcgctctgct aatcctgtta ccagtggctg   2760
ctgccagtgg cgataagtcg tgtcttaccg ggttggactc aagacgatag ttaccggata   2820
aggcgcagcg gtcgggctga acgggggtt cgtgcacaca gcccagcttg gagcgaacga    2880
cctacaccga actgagatac ctacagcgtg agctatgaga aagcgccacg cttcccgaag   2940
ggagaaaggc ggacaggtat ccggtaagcg gcagggtcgg aacaggagag cgcacgaggg   3000
agcttccagg gggaaacgcc tggtatcttt atagtcctgt cgggtttcgc cacctctgac   3060
ttgagcgtcg attttgtga tgctcgtcag ggggcggag cctatggaaa aacgccagca     3120
acgcggcctt tttacggttc ctggccttt gctggccttt tgctcacatg ttctttcctg    3180
cgttatcccc tgattctgtg gataaccgta ttaccgcctt tgagtgagct gataccgctc    3240
gccgcagccg aacgaccgag cgcagcgagt cagtgagcga ggaagcggaa ga           3292
```